(12) United States Patent
Schiltz et al.

(10) Patent No.: US 9,981,968 B2
(45) Date of Patent: May 29, 2018

(54) SUBSTITUTED PYRROLO[2,3-D]PYRIMIDINES FOR THE TREATMENT OF CANCER AND PROLIFERATIVE DISORDERS

(71) Applicant: Northwestern University, Evanston, IL (US)

(72) Inventors: Gary E. Schiltz, Naperville, IL (US); Karl A. Scheidt, Evanston, IL (US); Steven T. Rosen, Chicago, IL (US); Nancy L. Krett, Elk Grove Village, IL (US)

(73) Assignee: Northwestern University, Evanston, IL (US)

( * ) Notice: Subject to any disclaimer, the term of this patent is extended or adjusted under 35 U.S.C. 154(b) by 0 days. days.

(21) Appl. No.: 14/854,899

(22) Filed: Sep. 15, 2015

(65) Prior Publication Data

US 2016/0002252 A1    Jan. 7, 2016

Related U.S. Application Data

(63) Continuation-in-part of application No. PCT/US2014/030368, filed on Mar. 17, 2014.

(60) Provisional application No. 61/787,893, filed on Mar. 15, 2013.

(51) Int. Cl.
*A61K 31/519* (2006.01)
*C07D 487/04* (2006.01)

(52) U.S. Cl.
CPC ................... *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,229,453 | A | 10/1980 | Roth et al. |
| 5,254,687 | A | 10/1993 | Taylor et al. |
| 5,686,457 | A | 11/1997 | Traxler et al. |
| 5,869,485 | A | 2/1999 | Missbach |
| 6,051,577 | A | 4/2000 | Altmann |
| 6,066,732 | A | 5/2000 | Taylor et al. |
| 7,279,474 | B2 | 10/2007 | Capelli et al. |
| 7,358,250 | B2 | 4/2008 | Farthing et al. |
| 7,531,546 | B2 | 5/2009 | Irie et al. |
| 7,544,672 | B2 | 6/2009 | Kasibhatla et al. |
| 7,625,894 | B2 | 12/2009 | Caravatti et al. |
| 7,951,810 | B2 | 5/2011 | Critchley et al. |
| 7,951,812 | B2 | 5/2011 | Roberts et al. |
| 7,981,902 | B2 | 7/2011 | Gangjee |
| 8,093,229 | B2 | 1/2012 | Kasibhatla et al. |
| 8,183,248 | B2 | 5/2012 | Nagle et al. |
| 8,258,143 | B2 | 9/2012 | Gangjee et al. |
| 8,420,657 | B2 | 4/2013 | Gaul et al. |
| 8,501,752 | B2 | 8/2013 | Gangjee |
| 8,507,672 | B2 | 8/2013 | Harrison et al. |
| 8,580,802 | B2 | 11/2013 | Salituro et al. |
| 8,633,205 | B2 | 1/2014 | Ledeboer et al. |
| 2003/0018700 | A1 | 1/2003 | Giroti |
| 2010/0144705 | A1 | 6/2010 | Miller |

FOREIGN PATENT DOCUMENTS

| | | |
|---|---|---|
| DE | 1916050 | 10/1969 |
| DE | 1916011 | 3/1970 |
| DE | 2818676 | 11/1979 |
| HU | 9601559 | 2/1997 |
| JP | 2012116777 | 6/2012 |
| WO | 2005028434 | 3/2005 |
| WO | 2005105804 | 11/2005 |
| WO | 2007062399 | 5/2007 |
| WO | 2008006547 | 1/2008 |
| WO | 2010095663 | 8/2010 |
| WO | WO 2011145718 | * 11/2011 |
| WO | 2012012712 | 1/2012 |

OTHER PUBLICATIONS

Gonda et al. Efficient Copper-Catalyzed Trifluoromethylation of Aromatic and Heteroaromatic Iodides: The Beneficial Anchoring Effect of Borates Organic Letters (2014), 16(16), 4268-4271.*
RN 1097301-32-0 of CAPLUS of STN, 1998.*
Ji Y. et al., "Innate C—H trifluoromethylation of heterocycles," PNAS, 2011, 108; 14411-14415.
Gangjee et al., "Synthesis of 5,7-disubstituted-4-methyl-7H-pyrrolo[2,3-d]pyrimidin-2-amines as microtubule inhibitors", Bioorganic & Medicinal Chemistry, Mar. 1, 2013, 21(5):1180-1189.
Gangjee et al., "Design, synthesis, and x-ray crystal structure of a potent dual inhibitor of thymidylate synthase and dihydrofolate reductase as an antitumor agent", Journal of Medicinal Chemistry, 2000, 43(21):3837-3851.
International Preliminary Report on Patentability for PCT/US2014/030368 dated Sep. 24, 2015.
International Search Report for PCT/US2014/030368 dated Oct. 9, 2014.
Written Opinion for PCT/US2014/030368 dated Oct. 9, 2014.

* cited by examiner

*Primary Examiner* — Brian E McDowell
(74) *Attorney, Agent, or Firm* — Andrus Intellectual Property Law, LLP

(57) ABSTRACT

Disclosed are substituted pyrrolo[2,3-d]pyrimidine compounds. The disclosed compounds are shown to be useful in inhibiting the growth of cancer cell lines and treating cancer and cell proliferative disorders and have a general Formula I as indicated:

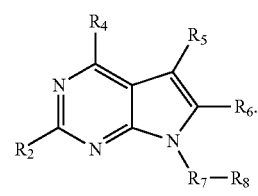

18 Claims, 17 Drawing Sheets

SUBSTITUTED PYRROLO[2,3-D]PYRIMIDINES FOR THE TREATMENT OF CANCER AND PROLIFERATIVE DISORDERS

CROSS-REFERENCE TO RELATED PATENT APPLICATIONS

The present application is a continuation-in-part under 35 U.S.C. § 365(c) of International Application PCT/US2014/030368, filed on Mar. 17, 2014, and published in English as WO 2014/145576 on Sep. 18, 2014, which claims the benefit of priority under 35 U.S.C. § 119(e) to U.S. Provisional Patent Application No. 61/787,893, filed on Mar. 15, 2013, the contents of which are incorporated herein by reference in their entireties.

BACKGROUND

The field of the invention relates to substituted pyrrolo[2,3-d]pyrimidines. In particular, the field of the invention relates to substituted pyrrolo[2,3-d]pyrimidines for the treatment of cell proliferation diseases and disorders such as cancer.

While treatment options have improved in recent years, cancer remains the second leading cause of death in the United States. Many cancers lack effective treatments and have poor long-term prognoses. In particular, multiple myeloma is the second most prevalent hematological malignancy and kills over 10,000 people annually. The median survival from this type of cancer is approximately 5-7 years. Even with the advent of several new chemotherapies, only 25-35% of patients respond to these drugs. Additional treatment options are necessary for patients who fail to respond to current therapies and for those who develop resistance to current therapies.

Here, as part of an effort to discover and evaluate new small molecules that have the potential for treating human cancer, in particular hematological malignancies, we have identified a series of novel substituted pyrrolo[2,3-d]pyrimidine compounds that display potent in vitro cytotoxicity against cancer cells. These compounds present unique substitution patterns that impart on them activity against a variety of human cancer cell lines. Compound analogs have been synthesized and tested to generate robust structure-activity relationships based on multiple sites of diversification. Lead compounds possess excellent profiles as potential therapeutics based on a variety of physiochemical properties. These new compounds therefore hold promise as new potential treatments for cancer and other proliferative diseases.

SUMMARY

Disclosed are substituted pyrrolo[2,3-d]pyrimidines. The disclosed compounds may be used in pharmaceutical compositions and methods for treating cell proliferative disorders such as cancer.

In some embodiments, the substituted pyrrolo[2,3-d]pyrimidines may have a Formula I:

wherein:
$R_2$ is hydrogen, halogen, or amino;
$R_4$ is hydrogen, hydroxyl, halogen, acetyl, amino, methylsulfonyl, acetyl, cyano, or $C_1$-$C_3$ alkyl optionally substituted at one or more positions with halogen;
$R_5$ and $R_6$ are each independently hydrogen, halogen, amino, or $C_1$-$C_3$ alkyl optionally substituted at one or more positions with halogen; or $R_5$ and $R_6$ are linked together to form a 6-membered ring, which optionally is a carbocyclic ring;
$R_7$ is N or $(CH_2)_n$ where n is 0, 1, 2, or 3;
$R_8$ is hydrogen, $C_1$-$C_3$ alkyl optionally substituted at one or more positions with halogen, $C_1$-$C_3$ alkoxy, amino, or a 4-, 5-, or 6-membered carbocyclic or heterocyclic ring that is saturated or unsaturated, the carbocyclic or heterocyclic ring optionally substituted at one or more carbon atoms with halogen, hydroxyl, methoxy, oxo, methylcarboxyl, methylamido, or methylhydroxyl; and the heterocyclic ring optionally substituted at a nitrogen heteroatom with a substituent selected from $C_1$-$C_3$ alkyl, or
$R_8$ is selected from In some embodiments. $R_8$ is a ring selected from piperidyl (e.g., N-piperidinyl, piperidin-2-yl), piperidin-3-yl, or piperidin-4-yl), phenyl, pyridinyl (e.g., pyridin-2-yl, pyridine-3-yl, or pyridine-4-yl) morpholino (e.g., N-morpholino), pyrrolidinyl (e.g., N-pyrrolidinyl, pyrrolidin-2-yl, or pyrrolidin-3-yl), 2-pyrrolidinonyl (e.g., N-2-pyrrolidinonyl), oxanyl (e.g., oxan-2-yl, oxan-3-yl, or oxan-4-yl), and ribosyl (e.g., D-ribosyl), which may be substituted as indicated above in Formula I or unsubstituted.

In particular, the compounds disclosed herein may have a Formula IA:

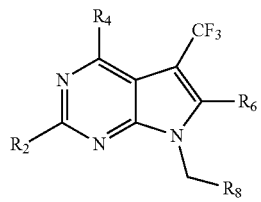

IA wherein: $R_4$ is hydrogen, halogen, or methyl; and $R_2$, $R_6$, and $R_8$ are as defined for Formula I. The compounds disclosed herein having Formula IA may include, but are not limited to:

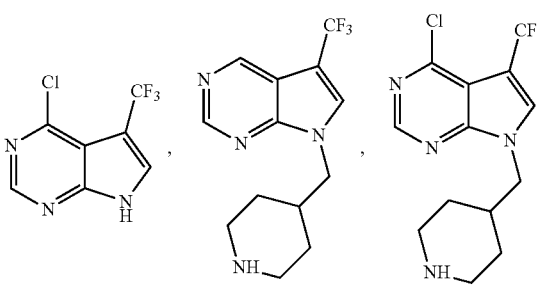

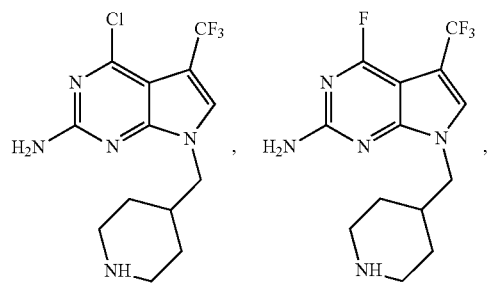

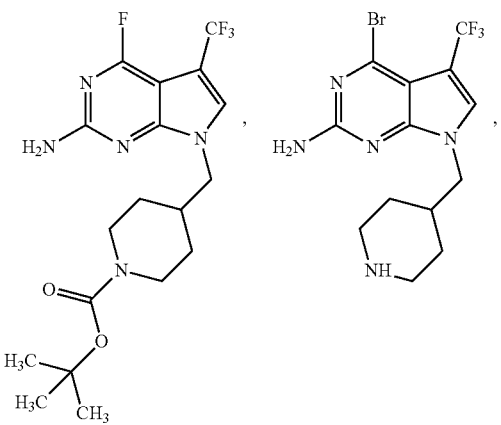

-continued

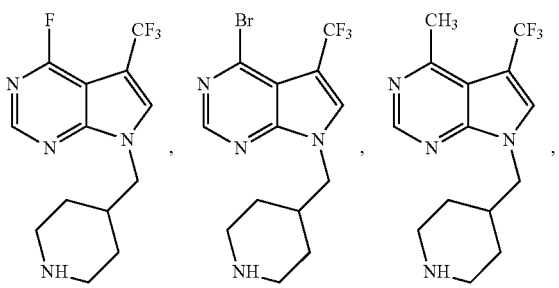

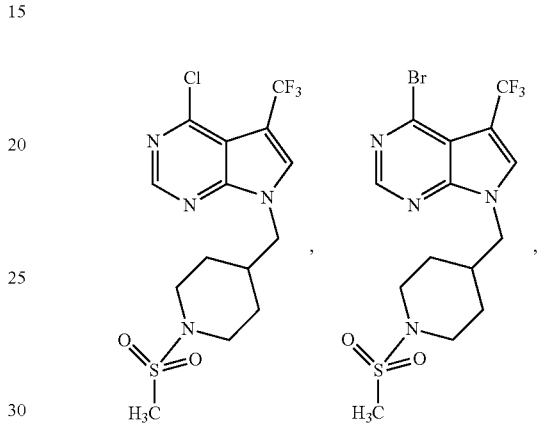

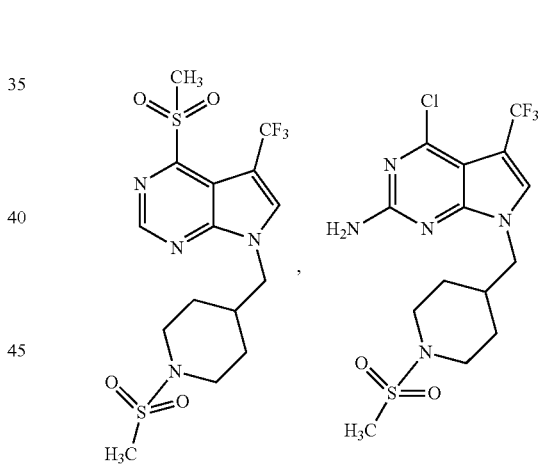

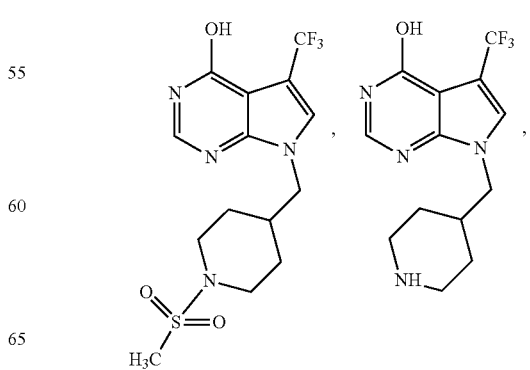

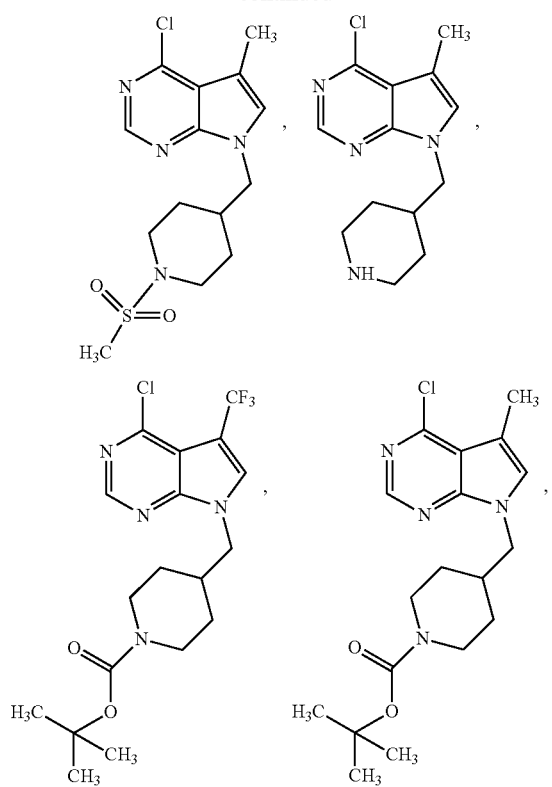
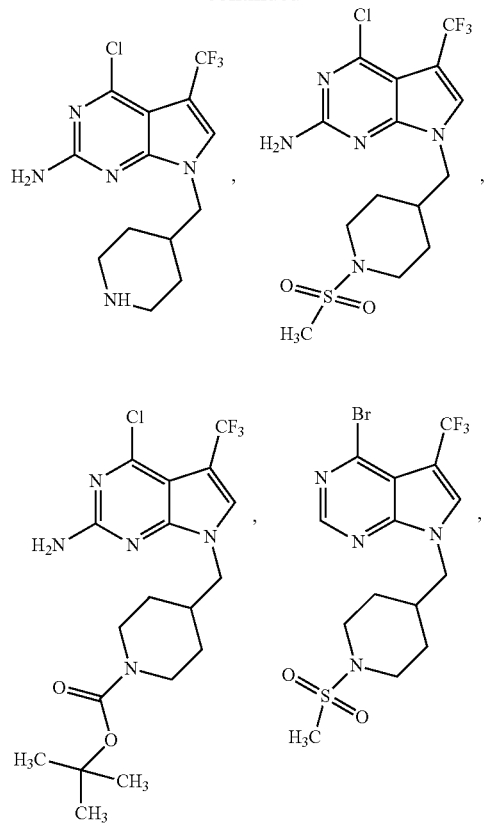
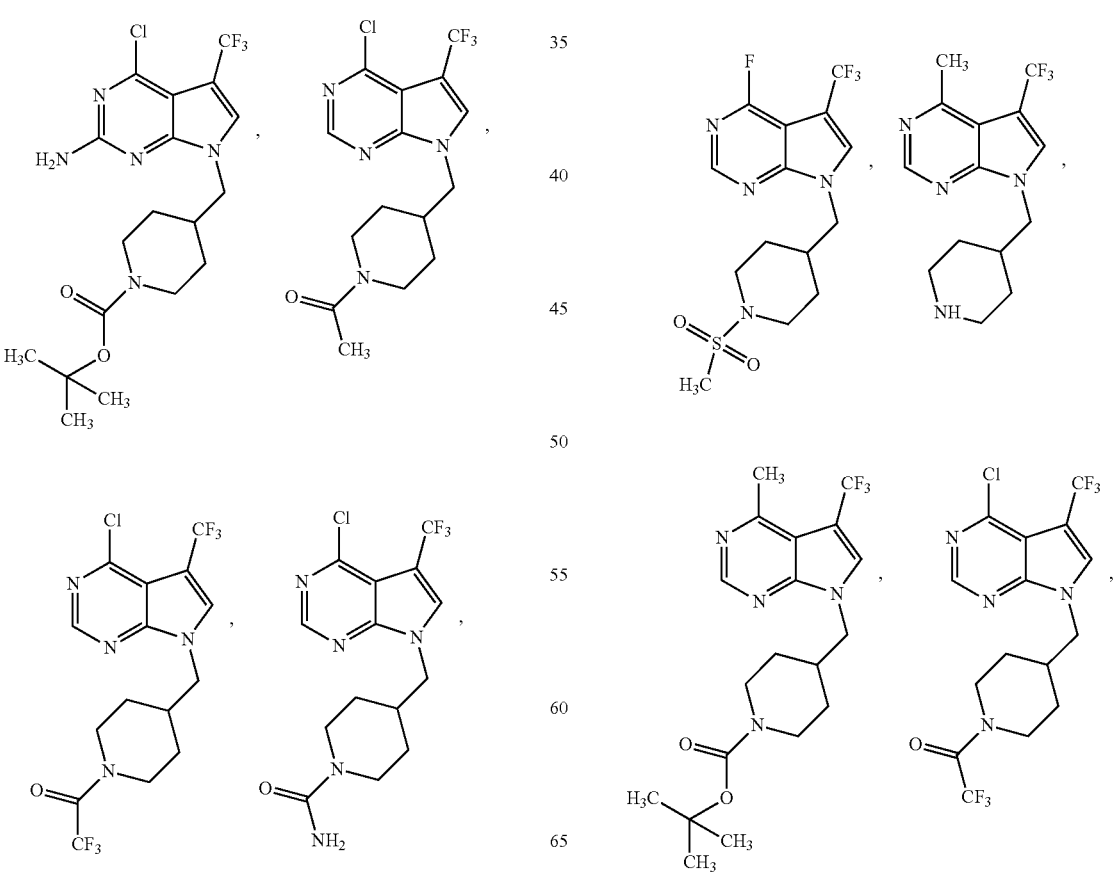

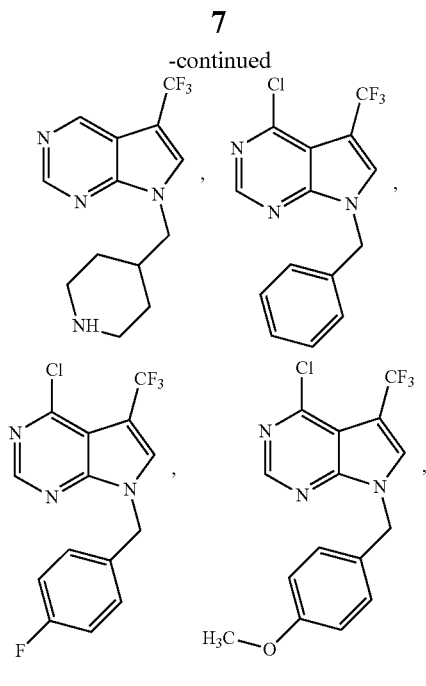
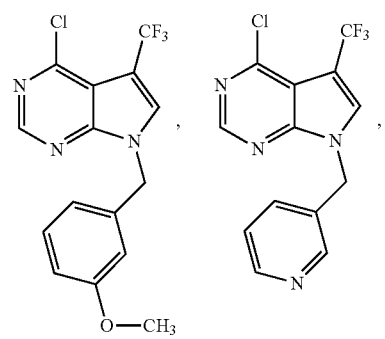
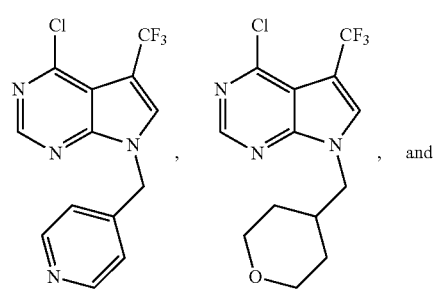
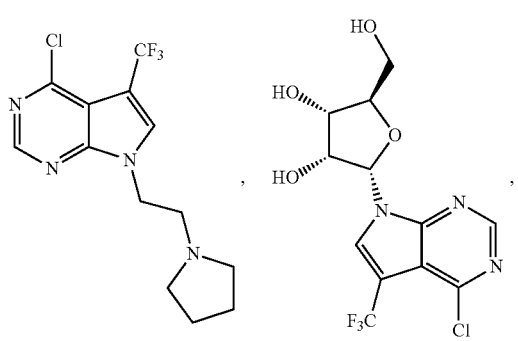

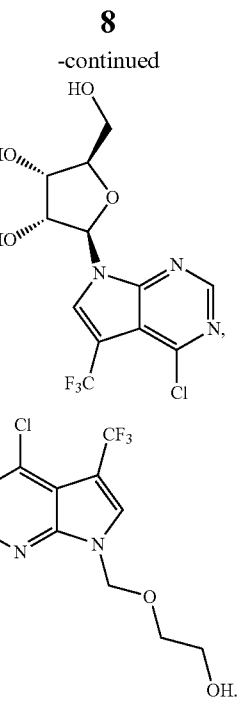

In particular, the compounds disclosed herein may have a Formula IB:

IB

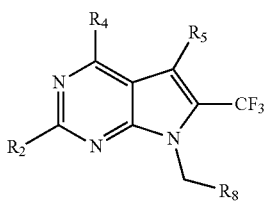

wherein: R₄ is hydrogen, halogen, methyl; and R₂, R₅, and R₈ are as defined for Formula I. In some embodiments, R₈ is a ring selected from piperidine, benzene, pyridine, pyrrolidine, and oxane, which may be substituted as indicated for Formula I or unsubstituted. The compounds disclosed herein having Formula IB may include, but are not limited to:

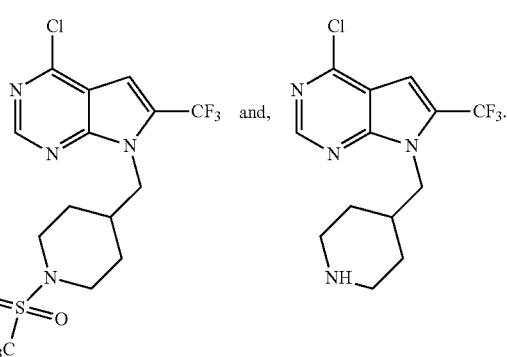

In particular, the compounds disclosed herein may have a Formula IC:

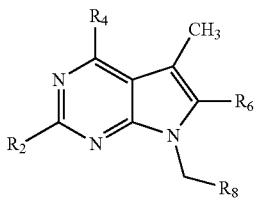

wherein: $R_4$ is hydrogen, halogen, or methyl; and $R_2$, $R_6$, and $R_8$ are as defined for Formula I. In some embodiments, $R_8$ is a ring selected from piperidine, benzene, pyridine, pyrrolidine and oxane, which may be substituted as indicated for Formula I or unsubstituted. The compounds disclosed herein having Formula IC may include, but are not limited to

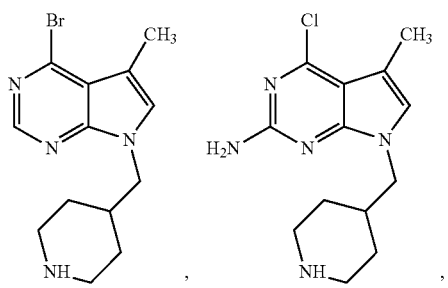

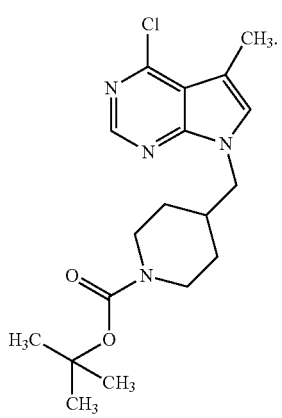

Other of the substituted pyrrolo[2,3-d]pyrimidine compounds disclosed herein may have a Formula ID:

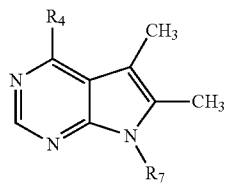

wherein $R_4$ is halogen or amine; and $R_7$ is as defined for Formula I. In some embodiments, $R_4$ is chlorine and $R_7$ is selected from

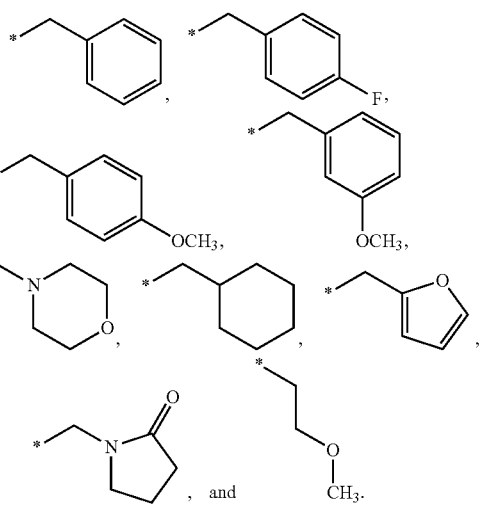

In other embodiments, the compounds disclosed herein having Formula ID may include, but are not limited to

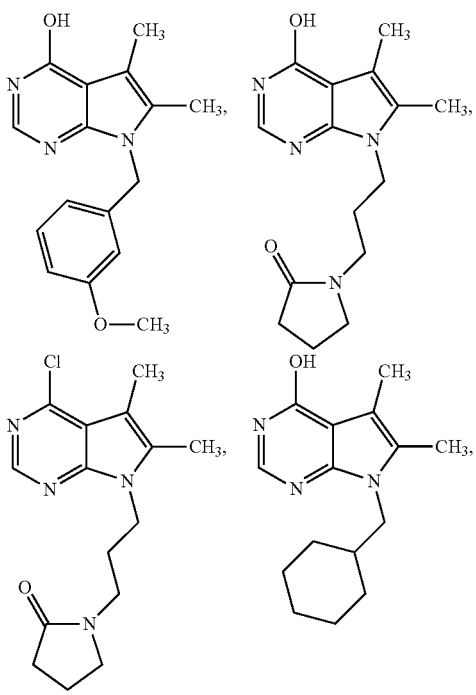

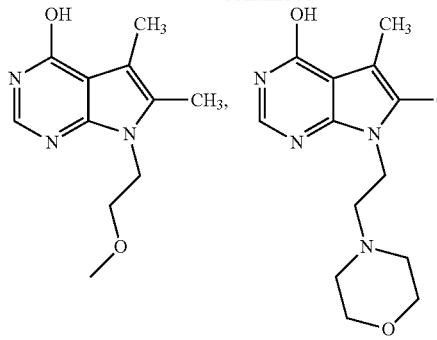

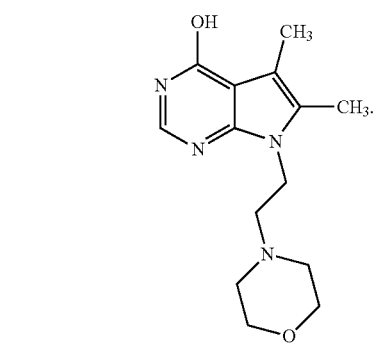

Other of the substituted pyrrolo[2,3-d]pyrimidine compounds disclosed herein may have a Formula IE may

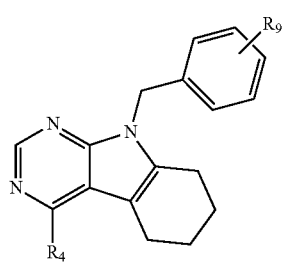

otherwise referred to as a "tricyclic 6,7,8,9-tetrahydro-5H-pyrimido[4,5-b]indole core," wherein: $R_4$ is halogen or hydroxyl; and $R_9$ is hydrogen, halogen, or methoxy. In some preferred embodiments, $R_4$ is chlorine. In other preferred embodiments, $R_9$ is halogen, and in particular, fluorine. The compounds disclosed herein having Formula ID may include, but are not limited to

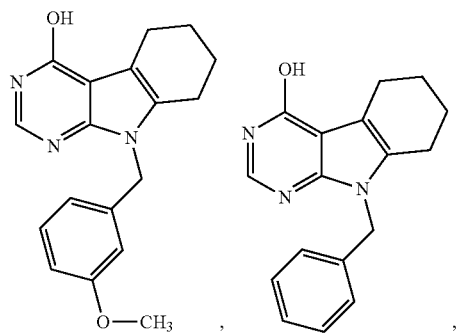

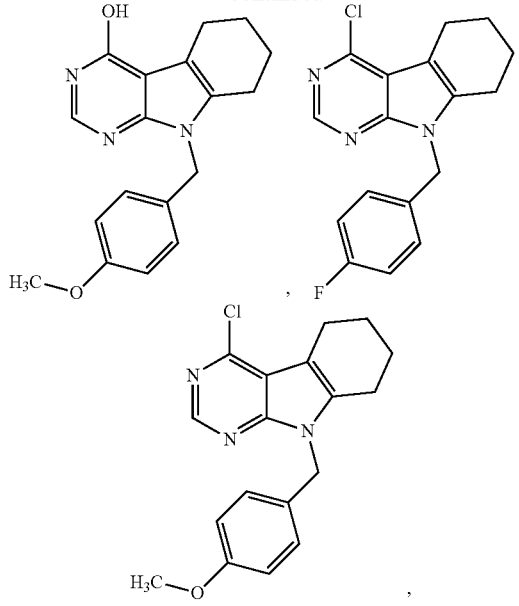

Other of the substituted pyrrolo[2,3-d]pyrimidine compound disclosed herein may have a Formula IF:

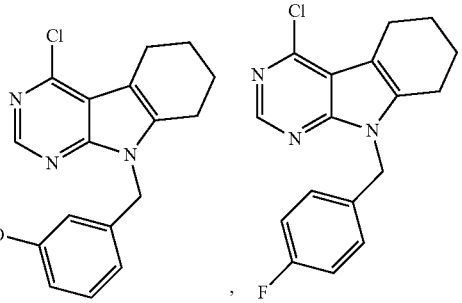

wherein: $R_2$ is hydrogen, halogen, or amino;
$R_4$ is halogen; and
$R_9$ is hydrogen, or is selected from

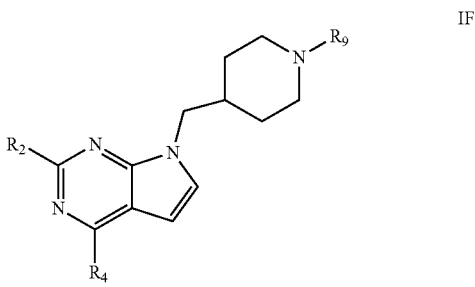

In some preferred embodiments, $R_4$ is chlorine. Specific compounds having Formula IF may include, but are not limited to:

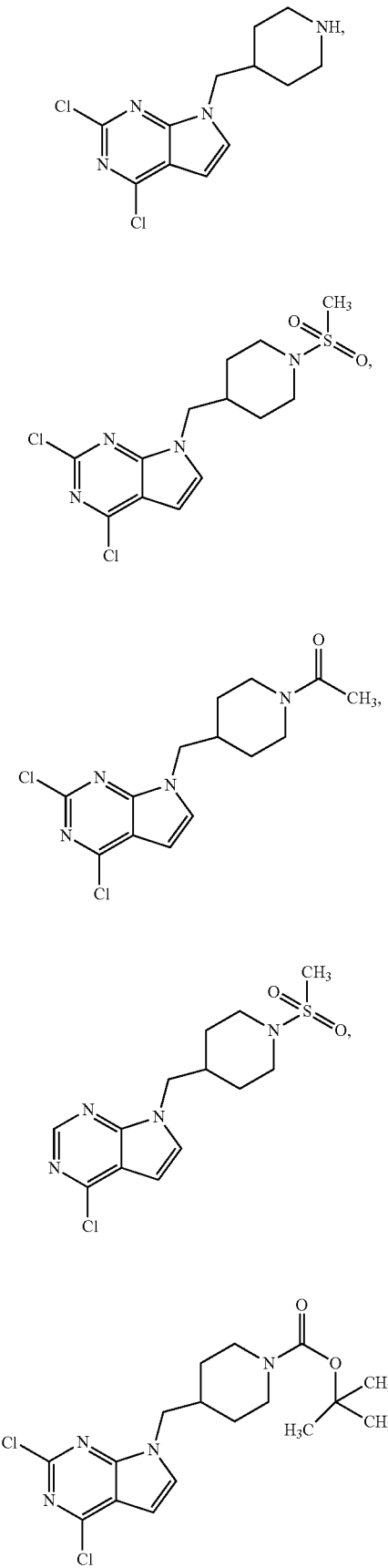

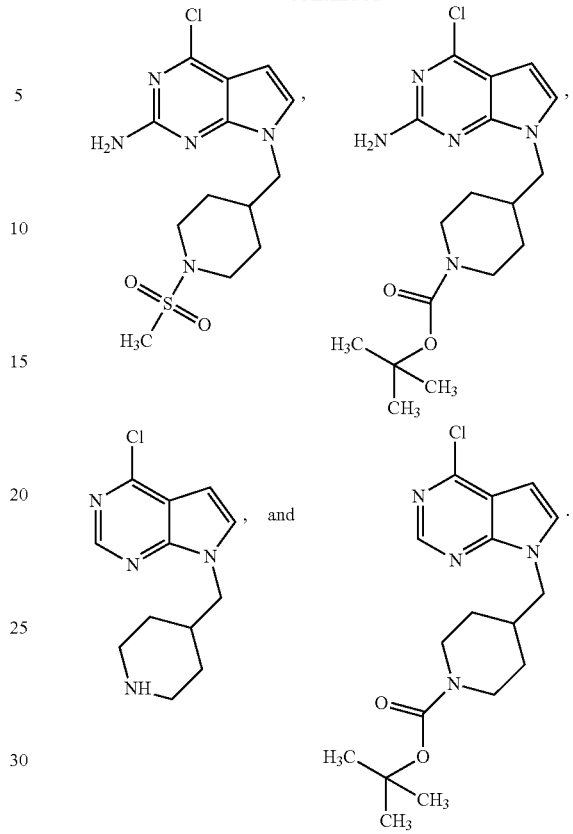

Also disclosed are pharmaceutical compositions that comprise the disclosed compounds together with a carrier, diluent, or excipient. The pharmaceutical compositions may comprise an effective amount of the compounds (or salts, esters, amides, or solvates thereof) for treating and/or preventing a disease, disorder, or condition which may include cell proliferation diseases, disorders, or conditions, such as cancer.

Also disclosed are methods of treating cancer that include administering the disclosed compounds, for example, where the compounds are formulated as a pharmaceutical composition and administered to a patient having cancer or suspected of having cancer. Cancers treated by the disclosed methods may include, but are not limited to multiple myeloma, leukemia, non-small cell lung cancer, colon cancer, cancer of the central nervous system, melanoma, ovarian cancer, renal cancer, prostate cancer, and breast cancer.

BRIEF DESCRIPTION OF THE DRAWINGS

FIG. 13. Inhibition of Kasumi-1 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).

DETAILED DESCRIPTION

Figure 1:
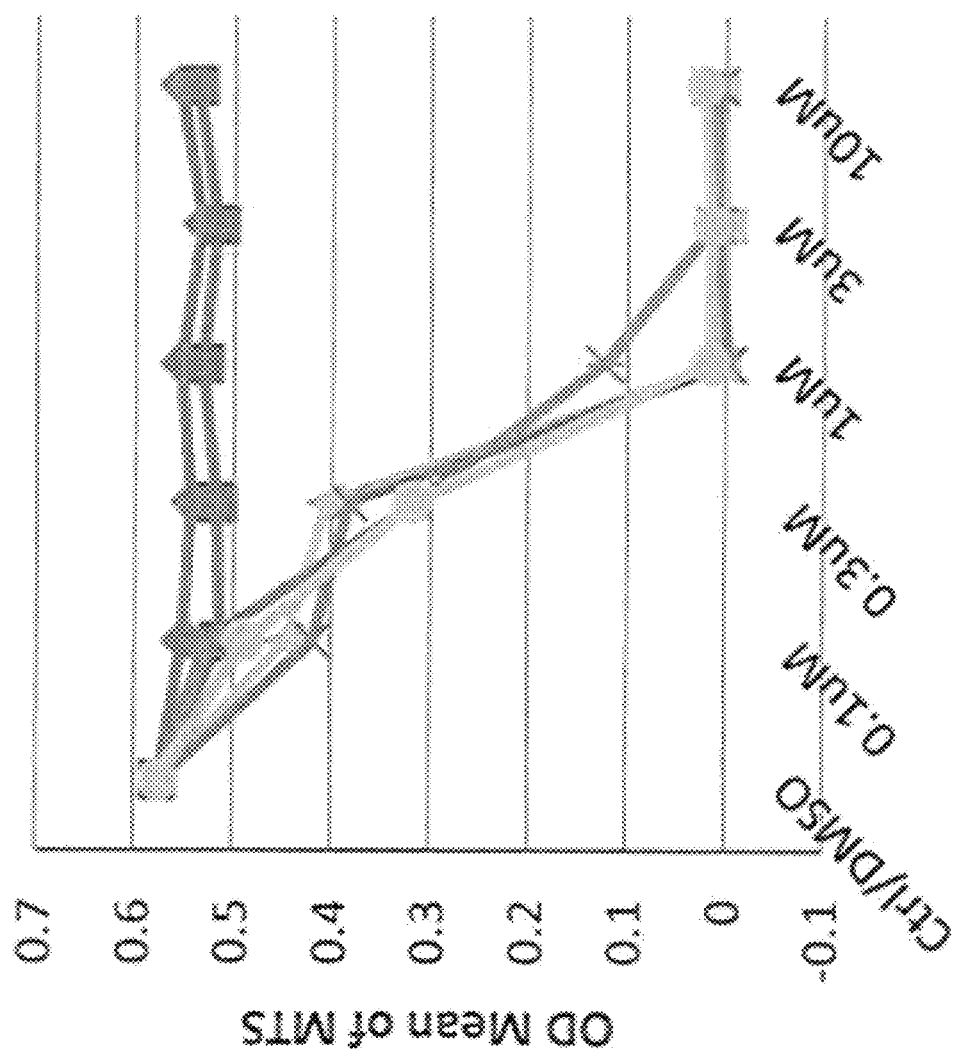
FIG. 1. Treatment of MM.1S cells with substituted pyrrolo[2,3-d]pyrimidine compounds or 8-amino adenosine.
Figure 2:
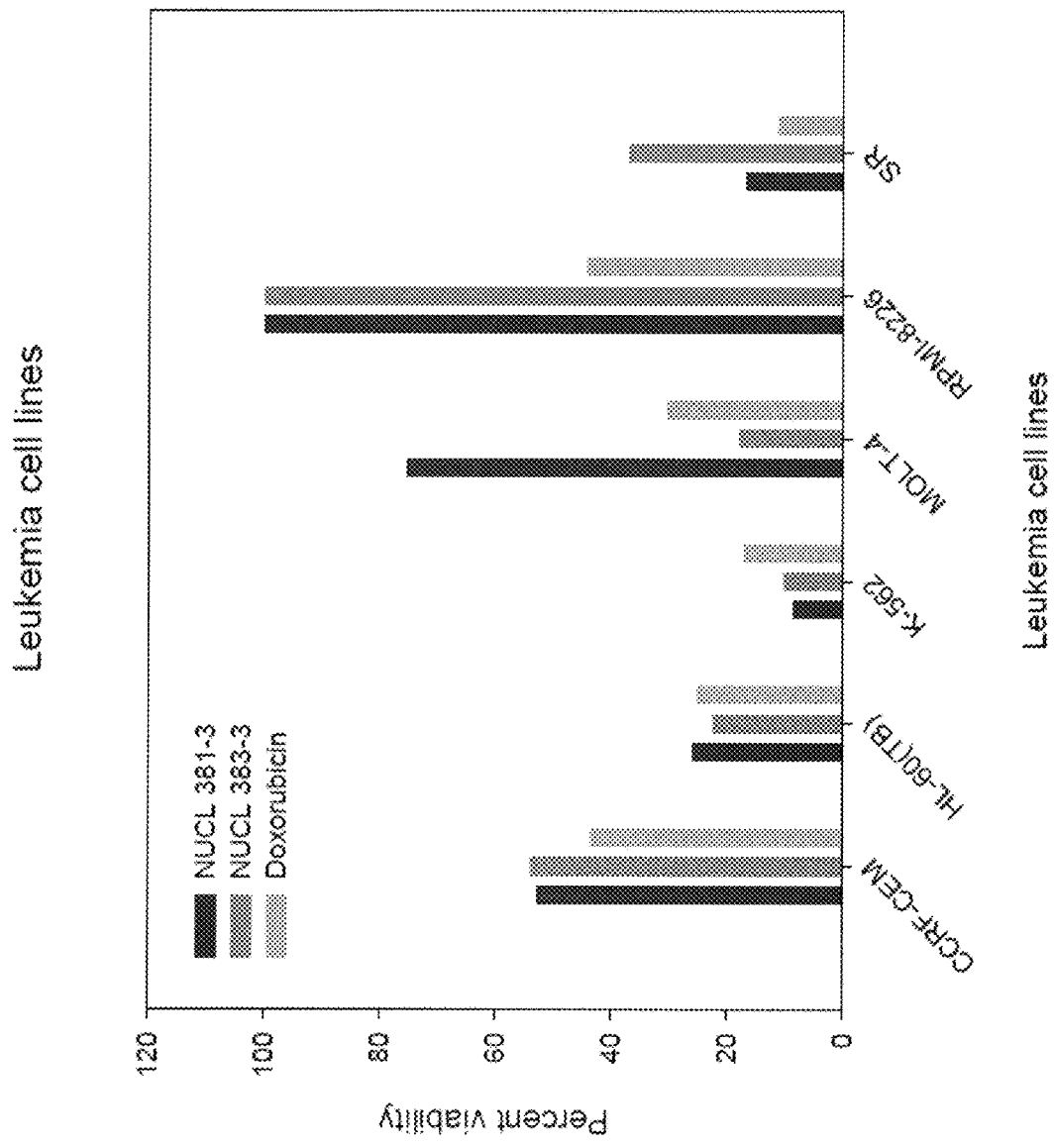
FIG. 2. Inhibition of leukemia cell lines by NUCL 381-3, NUCL 383-3, and Doxorubicin (left to right).
Figure 3:
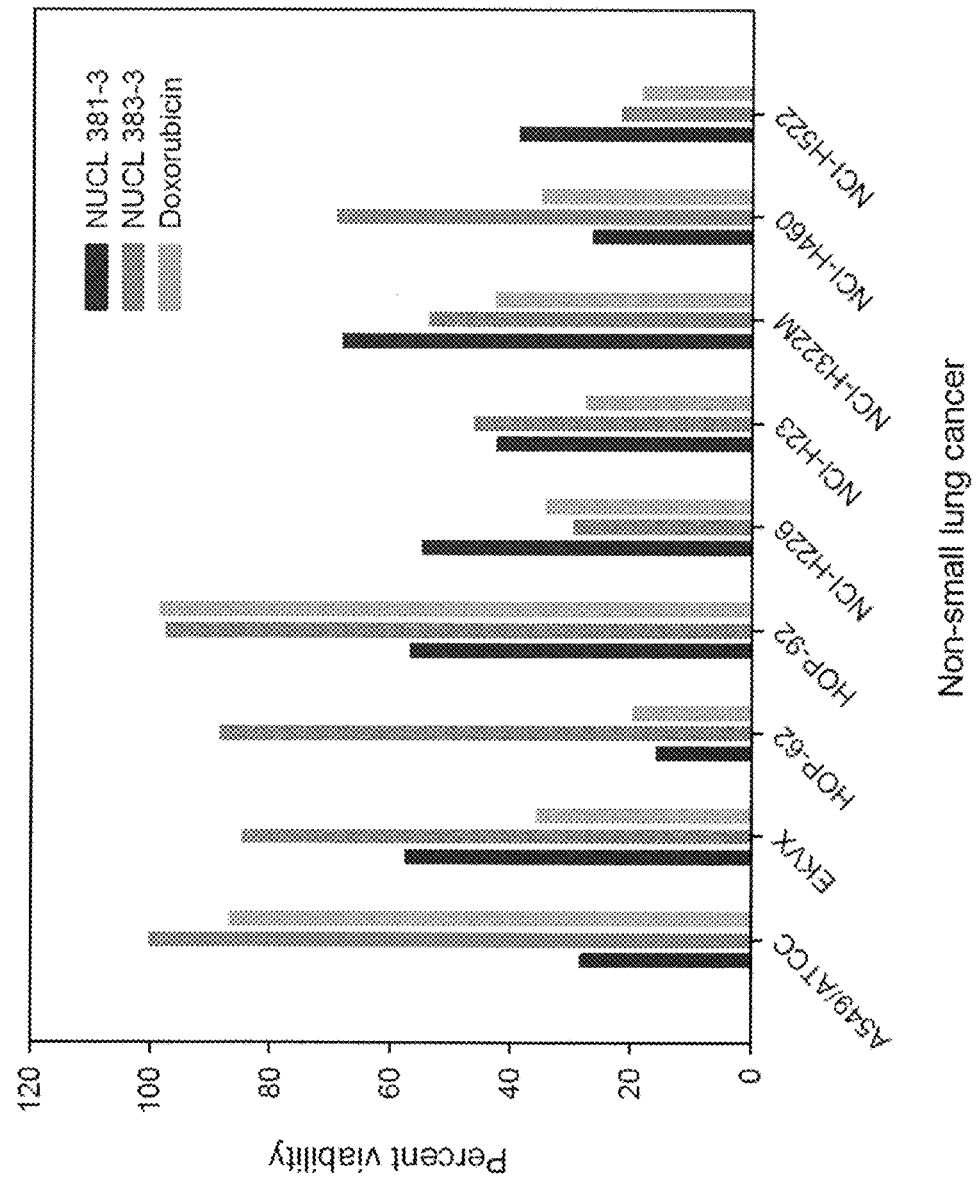
FIG. 3. Inhibition of non-small lung cancer cell lines by NUCL 381-3, NUCL 383-3, and Doxorubicin (left to right).
Figure 4:
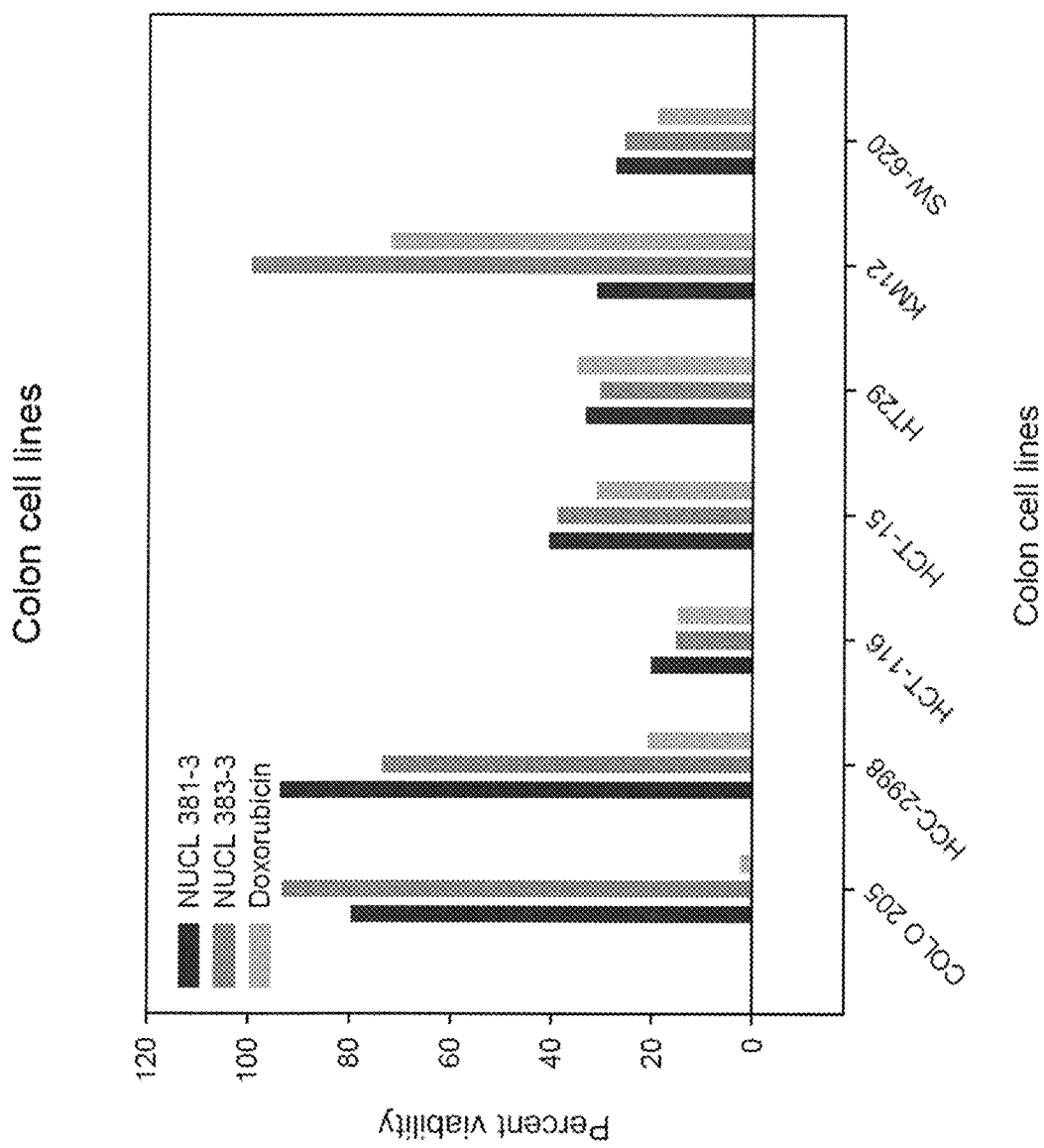
FIG. 4. Inhibition of colon cancer cell lines by NUCL 381-3, NUCL 383-3, and Doxorubicin (left to right).
Figure 5:
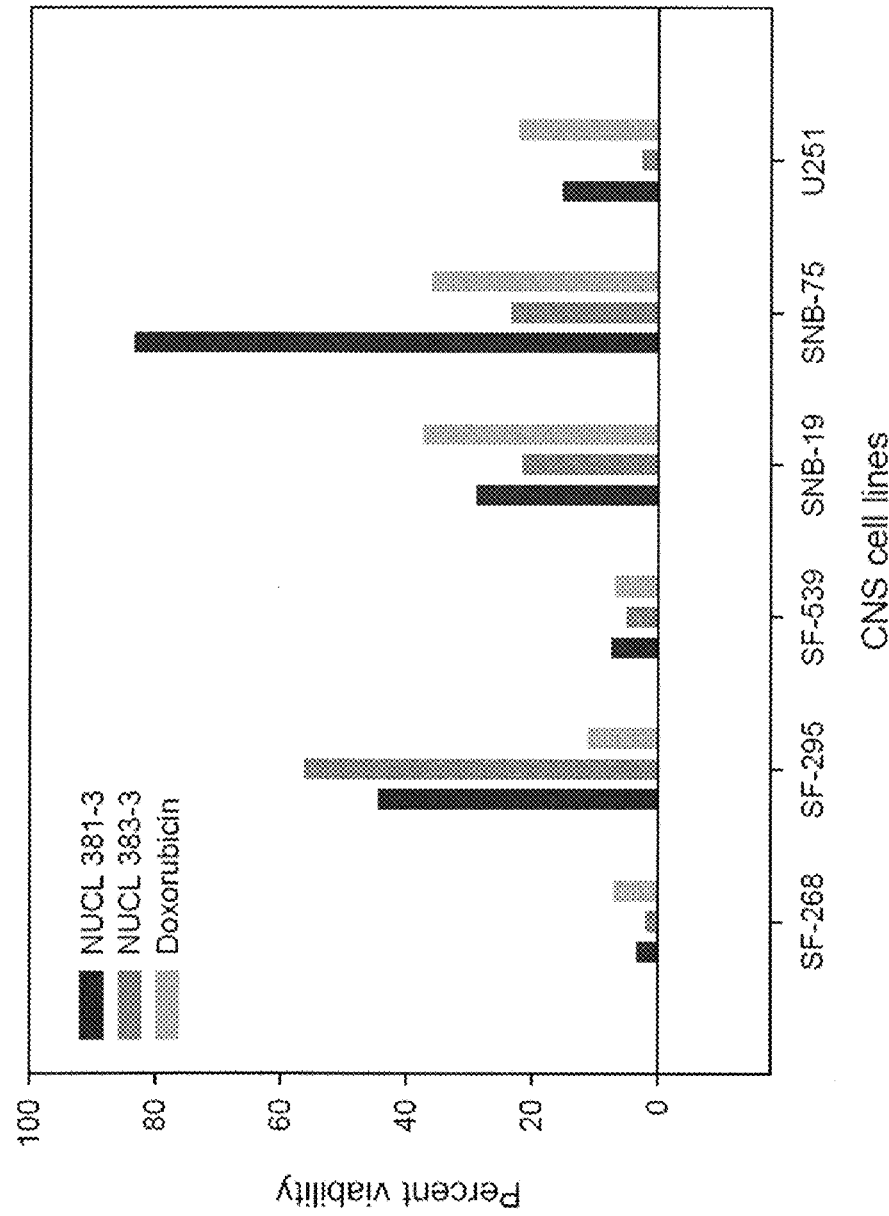
FIG. 5. Inhibition of central nervous system (CAN) cancer cell lines by NUCL 381-3, NUCL 383-3, and Doxorubicin (left to right).
Figure 6:
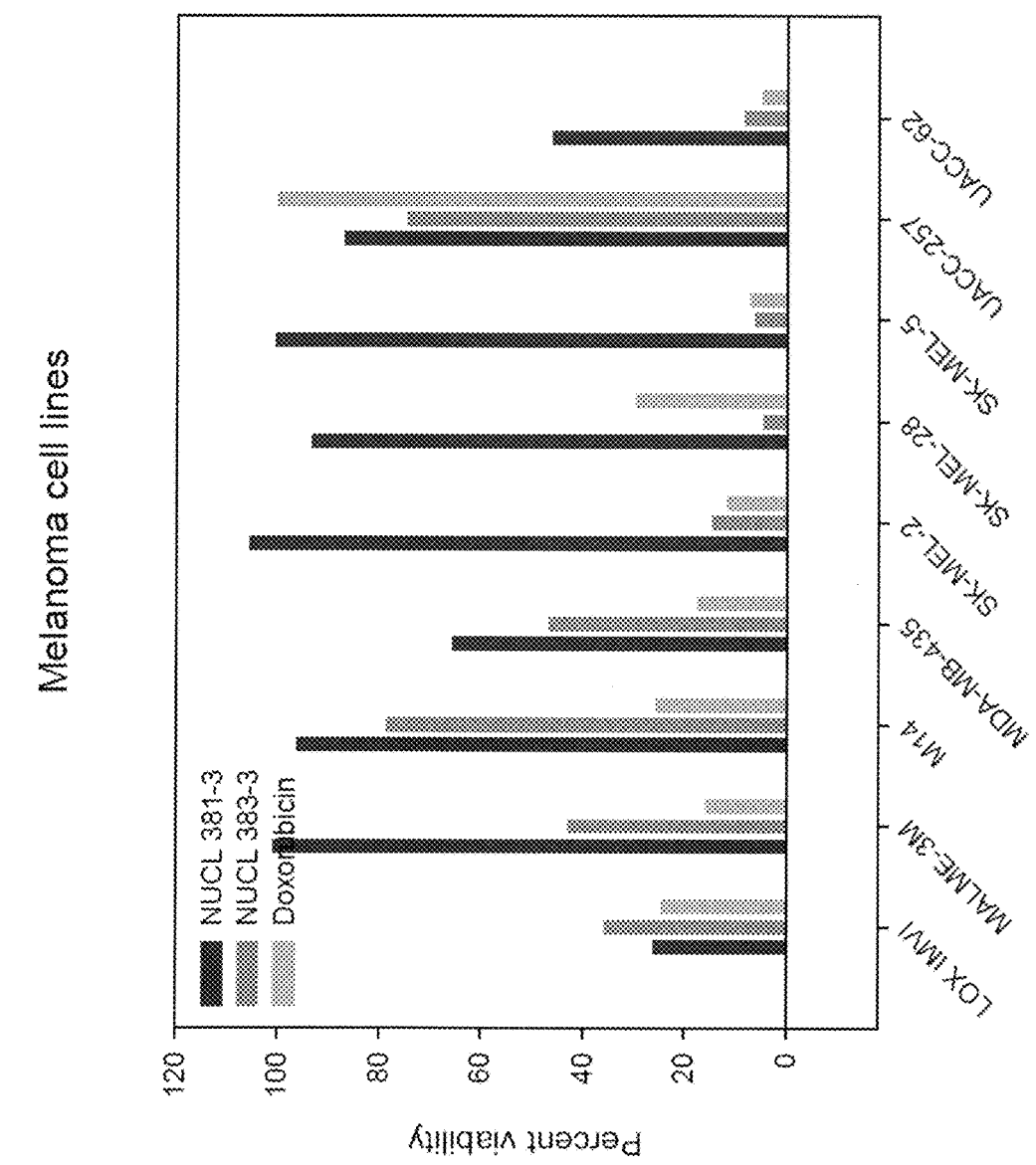
FIG. 6. Inhibition of melanoma cell lines by NUCL 381-3, NUCL 383-3, and Doxorubicin (left to right).
Figure 7:
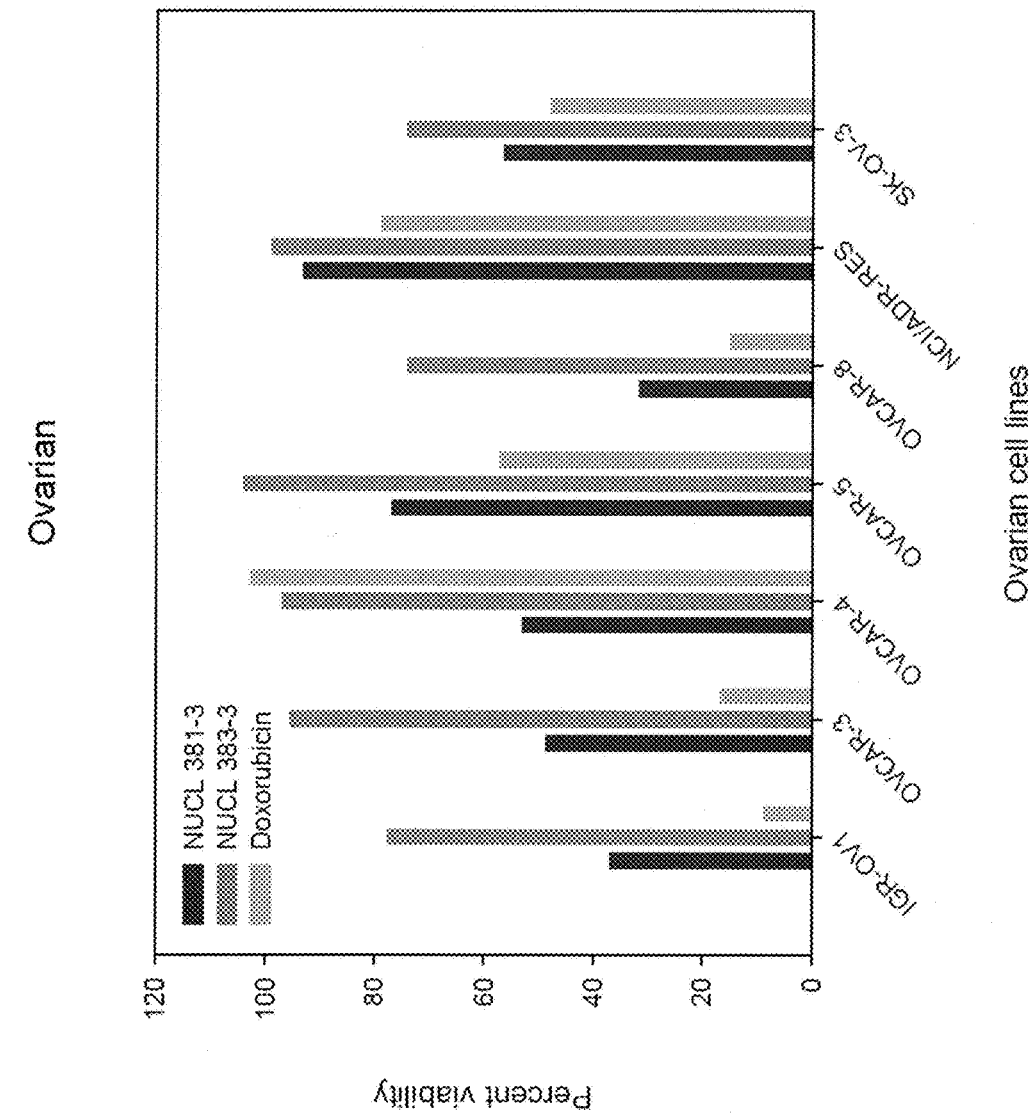
FIG. 7. Inhibition of ovarian cancer cell lines by NUCL 381-3, NUCL 383-3, and Doxorubicin (left to right).
Figure 8:
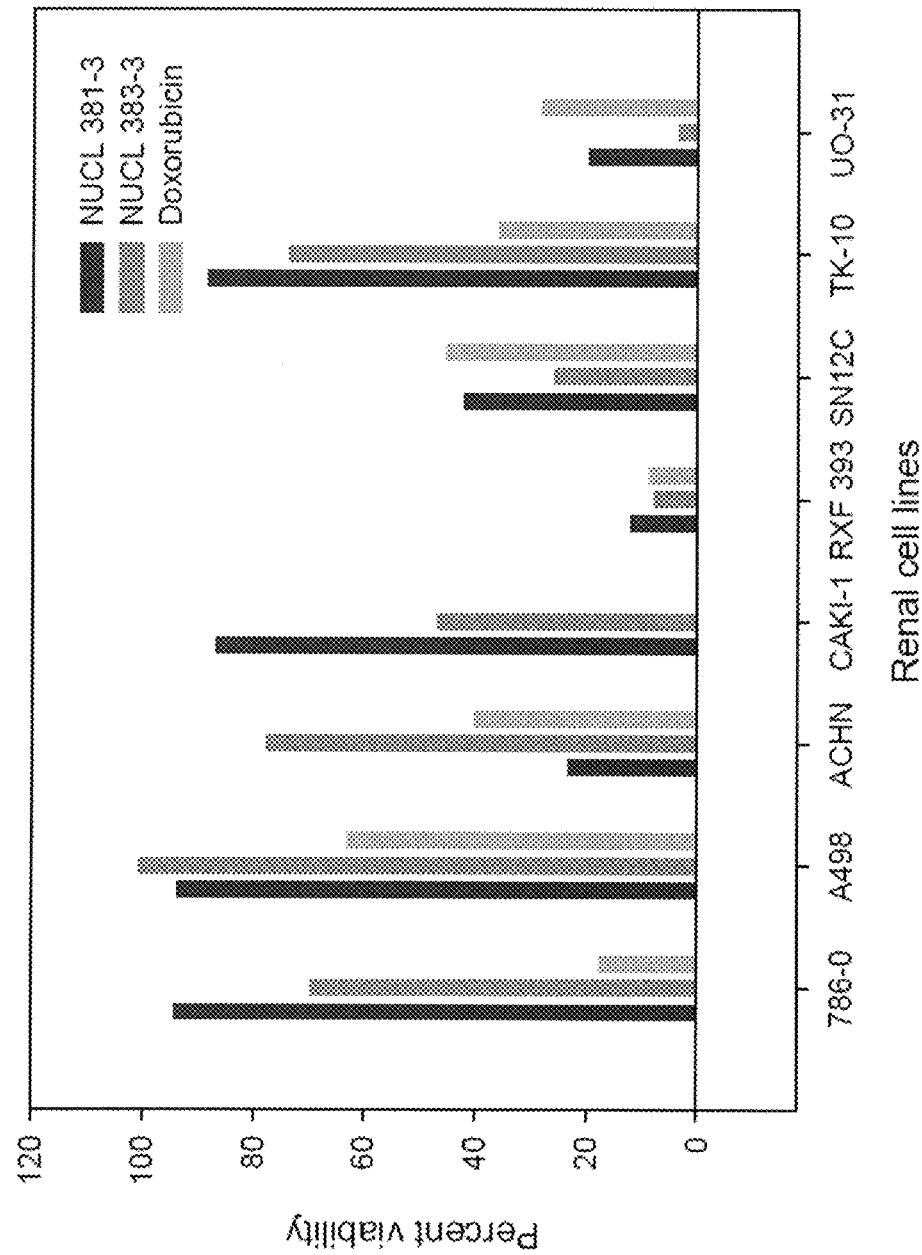
FIG. 8. Inhibition of renal cancer cell lines by NUCL 381-3, NUCL 383-3, and Doxorubicin (left to right).
Figure 9:
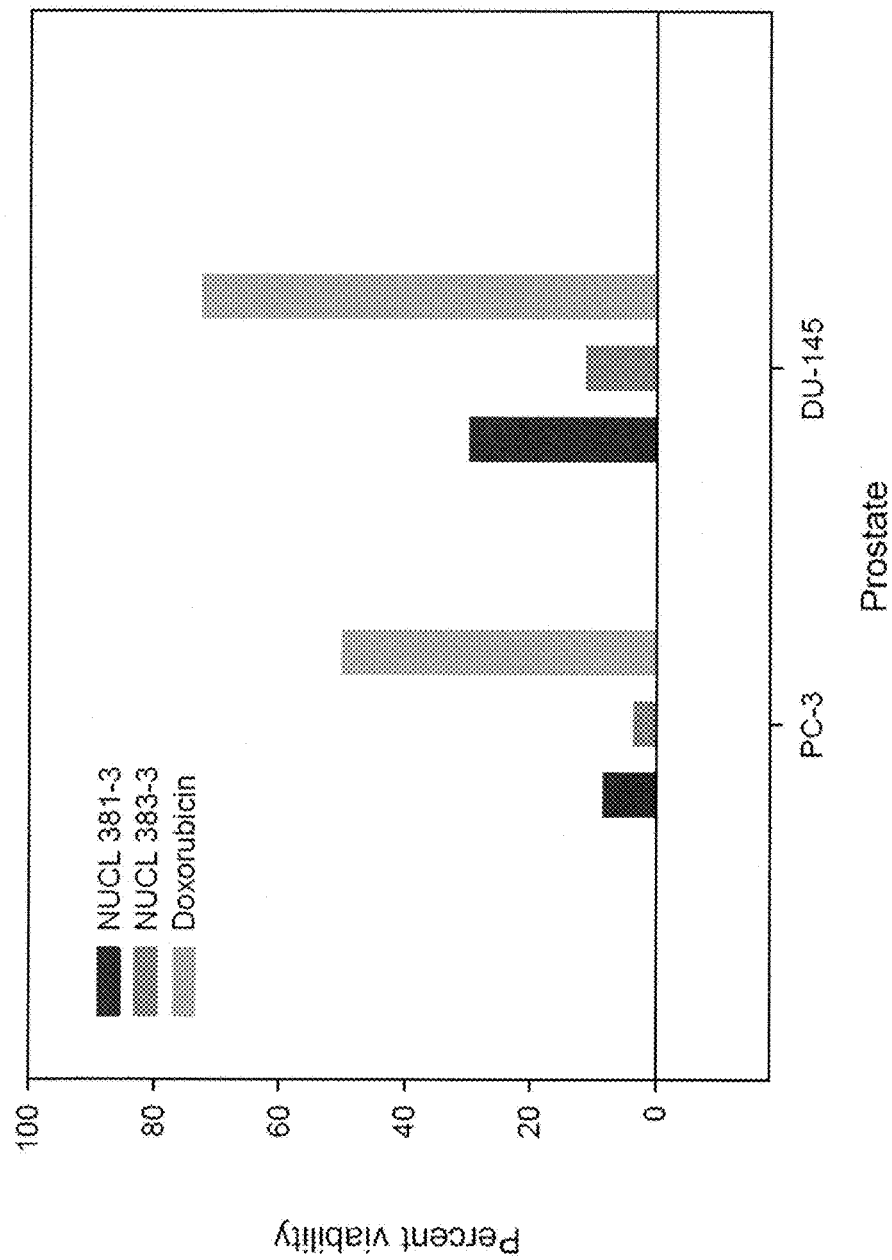
FIG. 9. Inhibition of prostate cancer cell lines by NUCL 381-3, NUCL 383-3, and Doxorubicin (left to right).
Figure 10:
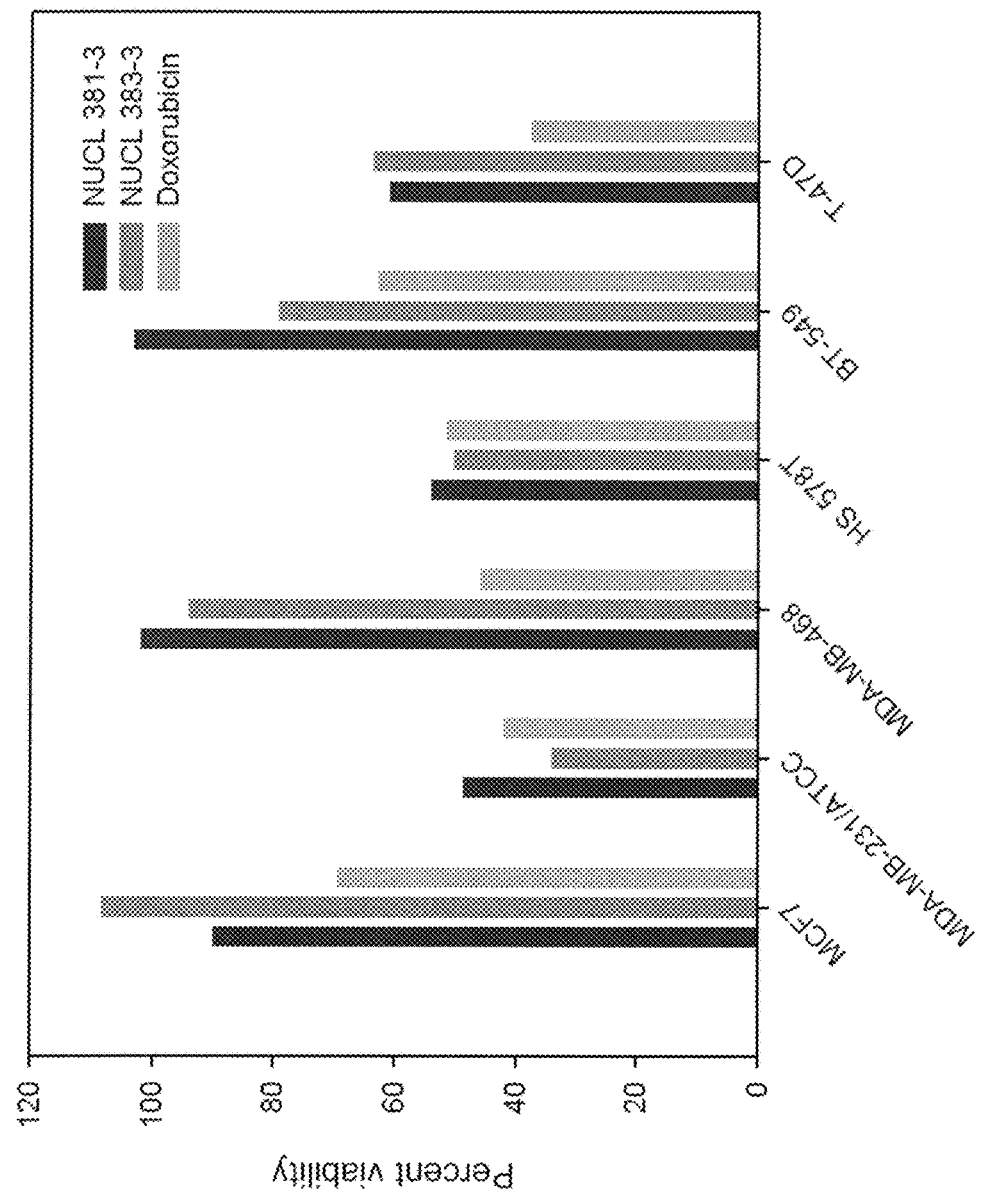
FIG. 10. Inhibition of breast cancer cell lines by NUCL 381-3, NUCL 383-3, and Doxorubicin (left to right).
Figure 11:
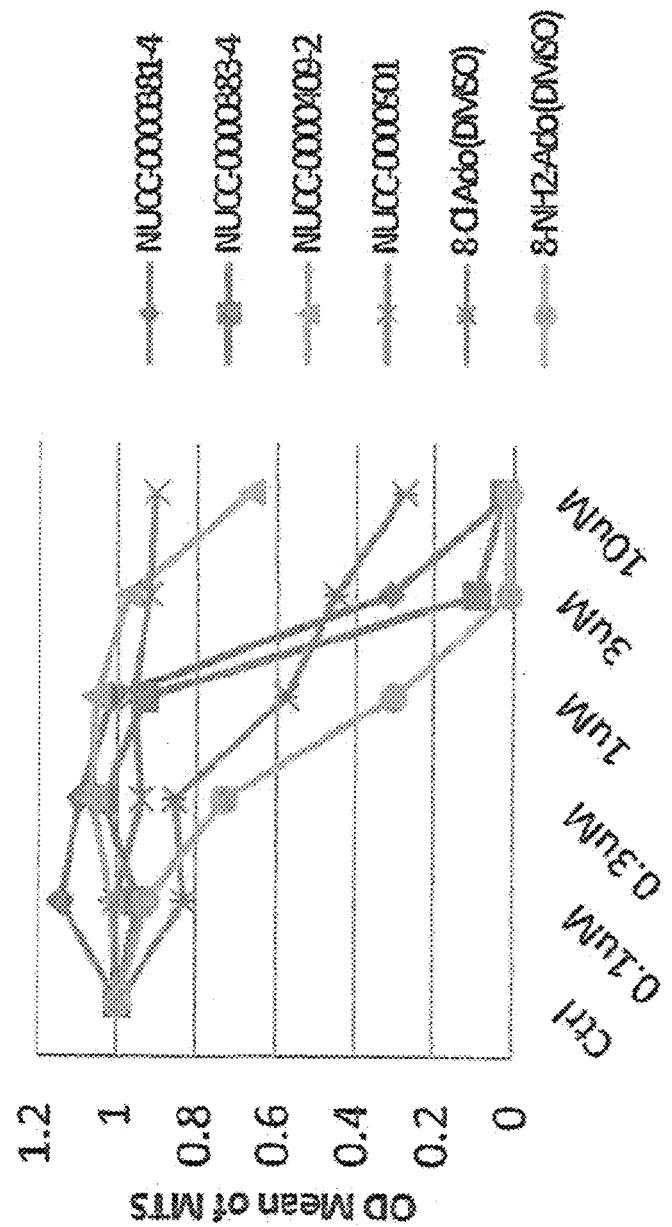
FIG. 11. Inhibition of THP-1 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).
Figure 12:
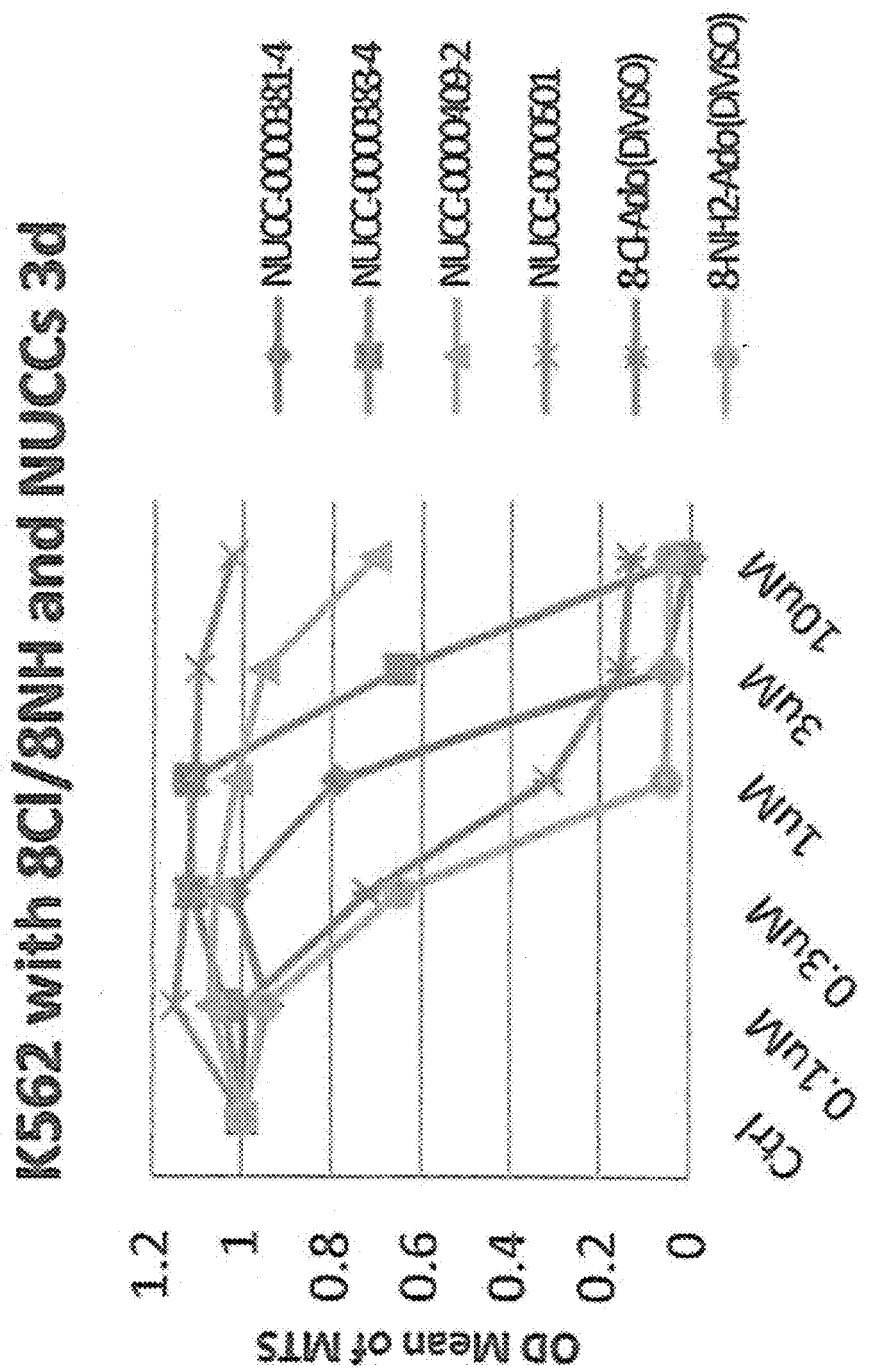
FIG. 12. Inhibition of K562 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).
Figure 13:
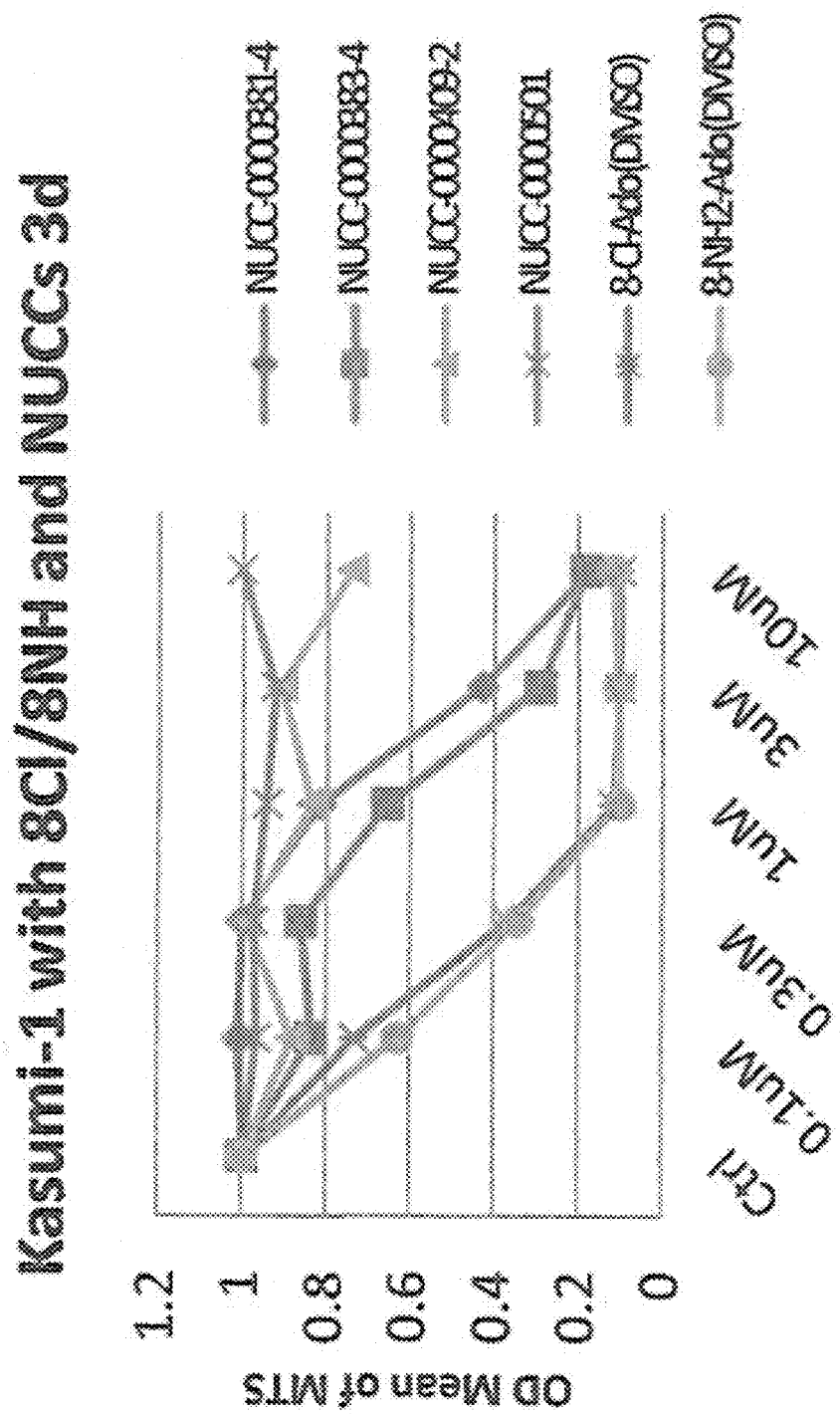
FIG. 13. Inhibition of Kasumi-1 cell lines.
Figure 14:
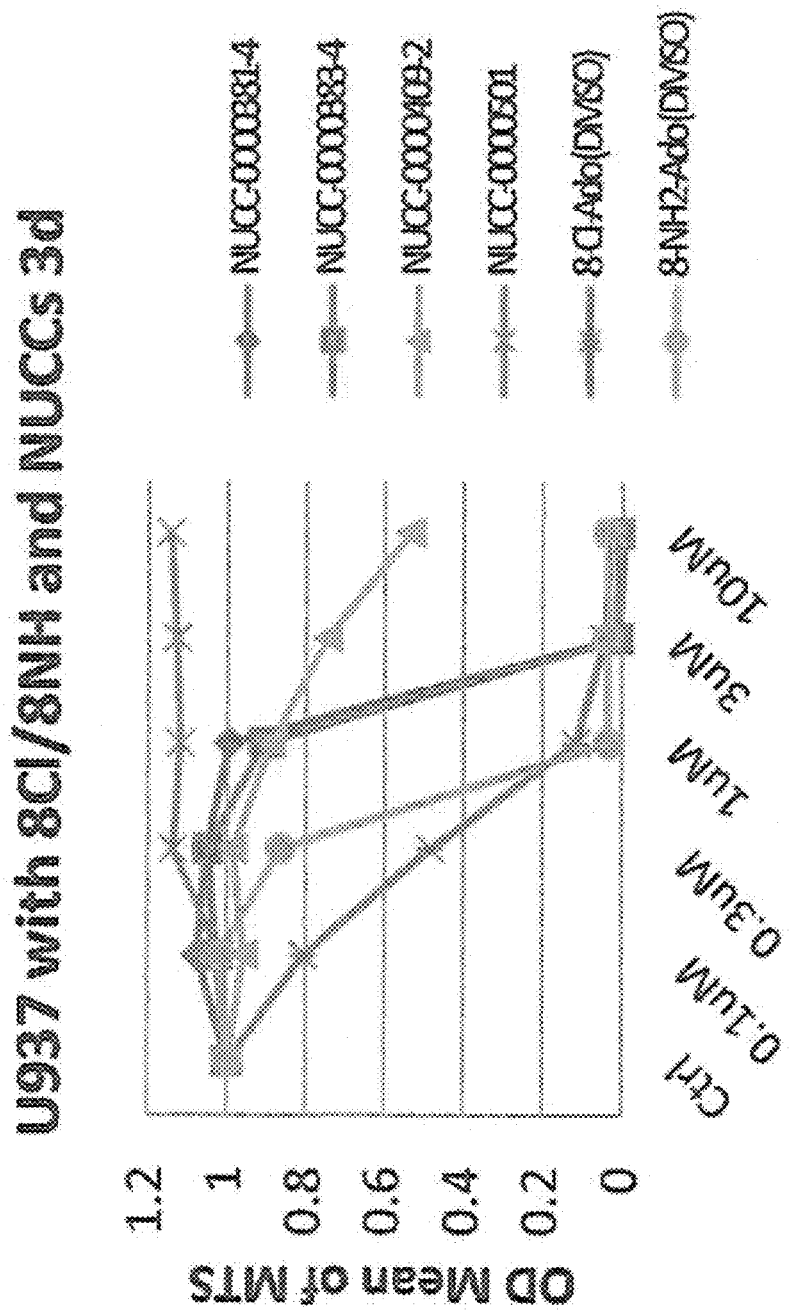
FIG. 14. Inhibition of U937 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).

The present invention is described herein using several definitions, as set forth below and throughout the application.

As used in this specification and the claims, the singular forms "a," "an," and "the" include plural forms unless the context clearly dictates otherwise. For example, the term "a compound" should be interpreted to mean "one or more compounds" unless the context clearly dictates otherwise. As used herein, the term "plurality" means "two or more."

As used herein. "about", "approximately." "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Disclosed herein are substituted pyrrolo-pyrimidine compounds that may be used for treatment of cancer and other proliferative disorders. The present invention is described herein using several definitions, as set forth below and throughout the application.

The term "alkyl" as contemplated herein includes a straight-chain or branched alkyl radical in all of its isomeric forms. Similarly, the term "alkoxy" refers to any alkyl radical which is attached via by an oxygen atom (i.e., a radical represented as "alkyl-O—*").

As used herein, an asterisk "*" is used to designate the point of attachment for any radical group or substituent group.

As used herein, a "patient" may be interchangeable with "subject" or "individual" and means an animal, which may be a human or non-human animal, in need of treatment.

A "patient in need of treatment" may include a patient having a disease, disorder, or condition that is responsive to therapy with a substituted pyrrolo[2,3-d]pyrimidine. For example, a "patient in need of treatment" may include a patient having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, and breast cancer).

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The formulae of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds.

The disclosed compounds may be effective in inhibiting cell proliferation of cancer cells. For example, the disclosed compound may be effective in inhibiting cell proliferation of one or more types of cancer cells including: multiple myeloma cells, such as MM.1S cells; leukemia cells, such as CCRF-CEM, HL-60(TB), MOLT-4, RPMI-8226 and SR; non-small lung cancer cells, such as A549/ATCC, EKVX, HOP-62, HOP-92, NCI-H226, NCI-H23, NCI-H322M, NCI-H460 and NCI-H522; colon cancer cells, such as COLO 205, HCC-2998, HCT-116, HCT-15, HT29, KM12 and SW-620; CNS: SF-268, SF-295, SF-539, SNB-19, SNB-75 and U251; melanoma cancer cells, such as LOX IMV1, MALME-3M, M14, MDA-MB-435, SK-MEL-2, SK-MEL-28, SK-MEL-5, UACC-257 and UACC-62; ovarian cancer cells, such as IGR-OV1, OVCAR-3, OVCAR-4, OVCAR-5, OVCAR-8, NCI/ADR-RES and SK-OV-3; renal cancer cells, such as 786-0, A498, ACHN, CAKI-1, RXF 393, SN12C, TK-10 and UO-31; prostate cancer cells, such as DU-145 and PC-3; and breast cancer cells, such as MCF7, MDA-MB-231/ATCC, MDA-MB-468, HS 578T, BT-549 and T-471).

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an IC50 of less than about 10 µM, 5 µM, 1 µM, or 0.5 µM in the selected assay.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel®, PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel®, PH102 lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream.

When formulated in an ointment, the compound may be employed with either a paraffinic or a water-miscible ointment base. Alternatively, the compound may be formulated in a cream with an oil-in-water cream base or a water-in-oil base.

Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, *acacia*, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or *acacia*; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

EXAMPLES

The following Examples are illustrative and are not intended to limit the scope of the claimed subject matter.

Example 1

Synthesis of Substituted Pyrrolo[2,3-d]pyrimidine Compounds

The synthesis and use of 5,6-disubstituted pyrrolo[2,3-d]pyrimidines are disclosed in the art. (See, e.g., patent document nos.: U.S. Pat. No. 8,633,205; U.S. Pat. No. 8,580,802; U.S. Pat. No. 8,507,672; U.S. Pat. No. 8,501,752; U.S. Pat. No. 8,420,657; U.S. Pat. No. 8,258,143; U.S. Pat. No. 8,183,248; U.S. Pat. No. 8,093,229; U.S. Pat. No. 7,981,902; U.S. Pat. No. 7,951,812; U.S. Pat. No. 7,951,810; U.S. Pat. No. 7,625,894; U.S. Pat. No. 7,544,672; U.S. Pat. No. 7,531,546; U.S. Pat. No. 7,358,250; U.S. Pat. No. 7,279,474; U.S. Pat. No. 6,066,732; U.S. Pat. No. 6,051,577; U.S. Pat. No. 5,869,485; U.S. Pat. No. 5,686,457; U.S. Pat. No. 5,254,687; U.S. Pat. No. 4,229,453; U.S. 2010/0144705; U.S. 2003/0018700; DE 2818676; DE 1916050; DE 1916011; WO 2012/012712; and WO 2008/006547; the contents of which are incorporated herein by reference in their entireties).

The presently disclosed substituted pyrrolo[2,3-d]pyrimidines may include a trifluoromethyl group. Trifluoromethylation of heterocycles is disclosed in Ji Y. et al., "Innate C—H trifluoromethylation of heterocycles," PNAS, 2011, 108; 14411-14415, the content of which is incorporated herein by reference in its entirety.

Synthesis

The substituted pyrrolo[2,3-d]pyrimidines disclosed herein may be synthesized using the following Schemes I and II:

Scheme I

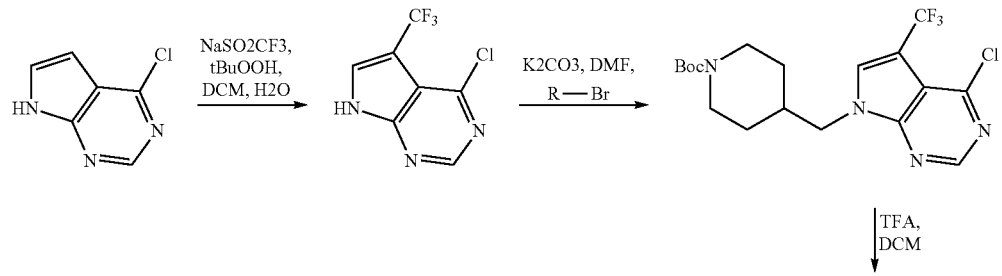

-continued

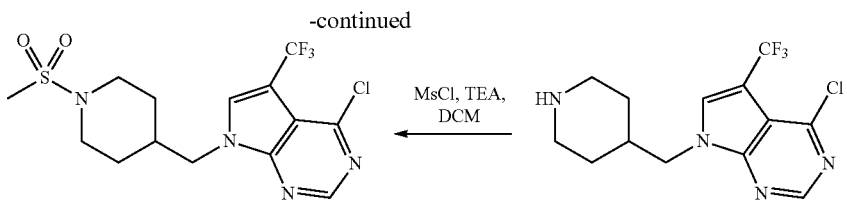

Scheme II

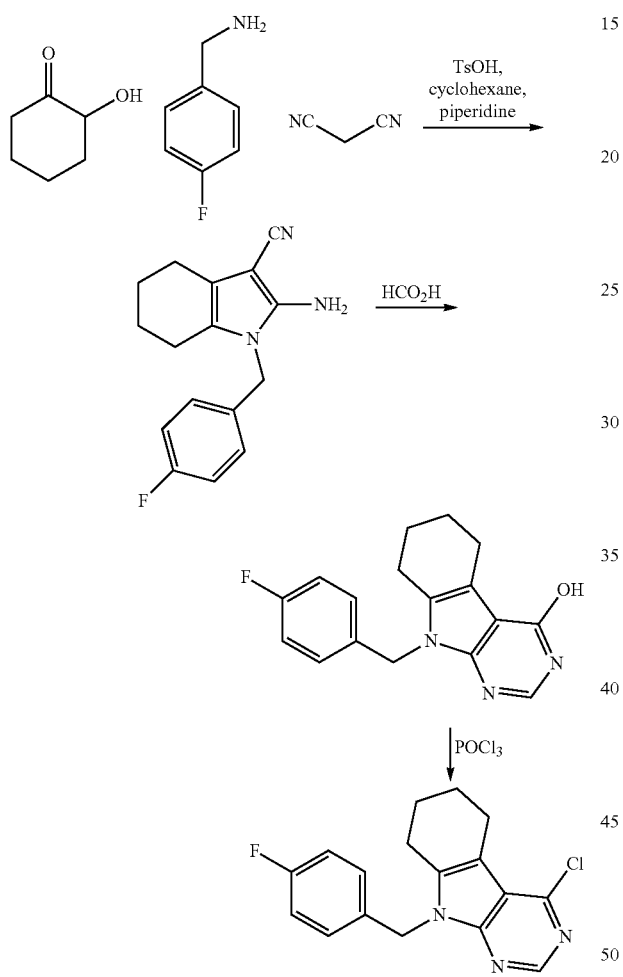

General Experimental

All chemical reagents were obtained from commercial suppliers and used without further purification unless otherwise stated. Anhydrous solvents were purchased from Sigma-Aldrich, and dried over 3 Å molecular sieves when necessary. DCM and THF were purified by passage through a bed of activated alumina. Normal-phase flash column chromatography was performed using Biotage KP-Sil 50 μm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light or iodine vapor. Liquid chromatography/mass spectrometry (LCMS) was performed on a Waters Acquity-H UPLC system with a 2.1 mm×50 mm, 1.7 μm, reversed phase BEH C18 column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). Proton ($^1$H) and carbon ($^{13}$C) NMR spectra were recorded on a Bruker Avance III w/direct cryoprobe spectrometer. Chemical shifts were reported in ppm (δ) and were referenced using residual non-deuterated solvent as an internal standard. The chemical shifts for $^1$H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. In some cases, overlapping signals occurred in the $^{13}$C NMR spectra.

Synthesis of 4-chloro-5-(trifluoromethyl)-7H-pyrrolo[2,3-d]pyrimidine

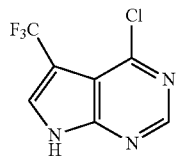

Into a 250 mL RBF were added 4-chloro-7H-pyrrolo[2,3-d]pyrimidine (1.0 g, 6.51 mmol) and DCM (25 ml), sodium trifluoromethylsulfinate (3.05 g, 19.54 mmol) and water (10 ml). The mixture was cooled to 0° C. To this was added tert-butyl hydroperoxide (4.5 ml, 32.6 mmol) dropwise over 15 min and the resulting mixture was stirred at RT for 3 days. Added 50 mL of sat. aq. NaHCO$_3$ and separated the layers. Extracted the aqueous with 2×50 mL with DCM. Combined the organics and washed with brine (100 mL), dried over Na$_2$SO$_4$, filtered, and concentrated. Purified by Biotage flash chrom, 50 g SiO2, eluting with 0-50% EA/Hex. Obtained the title compound as a white solid (0.34 g, 23%). MS (ESI): mass calcd. for C$_7$H$_3$ClF$_3$N$_3$, 221.00; m/z found, 222.1 [M+H]+; $^1$H NMR (500 MHz, CDCl$_3$) δ 7.09 (s, 1H), 8.81 (s, 1H), 12.09 (bs, 1H).

Synthesis of tert-butyl 4-((4-chloro-5-(trifluoromethyl)-7H-pyrrolo[2,3-d]pyrimidin-7-yl)methyl)piperidine-1-carboxylate

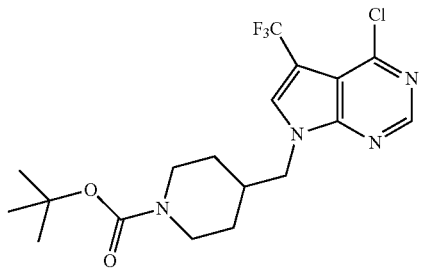 [SMILES: CC(C)(C)OC(=O)N1CCC(Cn2cc(C(F)(F)F)c3c(Cl)ncnc32)CC1]

Into an 8 mL vial were added 4-chloro-5-(trifluoromethyl)-7H-pyrrolo[2,3-d]pyrimidine (76 mg, 0.343 mmol), K2CO3 (166 mg, 1.201 mmol), DMF (1 mL), and tert-butyl 4-(bromomethyl)piperidine-1-carboxylate (239 mg, 0.858 mmol). The orange suspension was stirred at 80° C. for 6 hrs and then RT for 18 hrs. The suspension was concentrated and purified by Biotage flash chrom, 10 g SiO2, 0-30% EA/Hex to afford the title compound as a colorless oil. (70.1 mg, 49%). MS (ESI): mass calcd. for $C_{18}H_2ClF_3N_4O_2$, 418.14; m/z found, 419.1 [M+H]+; $^1$H NMR (500 MHz, CDCl$_3$) δ 8.76 (s, 1H), 7.08 (s, 1H), 4.27 (d, J=7.57 Hz, 2H), 4.13 (bs, 2H), 2.62 (bs, 2H), 2.24-2.22 (m, 1H), 1.46-1.45 (m, 2H), 1.45 (s, 9H), 1.33-1.29 (m, 2H).

Synthesis of 4-chloro-7-(piperidin-4-ylmethyl)-5-(trifluoromethyl)-7H-pyrrolo[2,3-d]pyrimidine

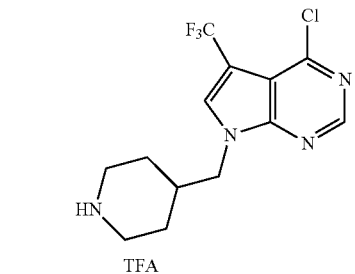 [SMILES: FC(F)(F)c1cn(CC2CCNCC2)c2ncnc(Cl)c12]

TFA

Into an 8 m vial were added tert-butyl 4-((4-chloro-5-(trifluoromethyl)-7H-pyrrolo[2,3-d]pyrimidin-7-yl)methyl)piperidine-1-carboxylate (55 mg, 0.131 mmol), DCM (1 ml), and TFA (0.5 ml, 0.131 mmol) and the reaction was stirred at RT for 30 min and then concentrated under a stream of nitrogen and then high vacuum. 2 mL of ether was added followed by sonication to produce a white solid. The ether was decanted and the solid under high vacuum for 30 min to afford the title compound as a white solid (37.5 mg, 94%). MS (ESI): mass calcd. for $C_{11}H_{14}ClF_3N_4$, 318.09; m/z found, 319.2 [M+H]+; $^1$H NMR (500 MHz, DMSO-d$_6$) δ 8.89 (s, 1H), 8.52 (bs, 1H), 8.18 (bs, 1H), 7.51 (d, J=0.95 Hz, 1H), 4.29 (d, J=7.88 Hz, 2H), 3.26-3.23 (m, 2H), 2.81 (d, J=11.03 Hz, 2H), 2.20-2.33 (m, 1H), 1.60 (d, J=13.24 Hz, 2H), 1.45-1.43 (m, 2H).

Synthesis of 4-chloro-7-((1-(methylsulfonyl)piperidin-4-yl)methyl)-5-(trifluoromethyl)-7H-pyrrolo[2,3-d]pyrimidine

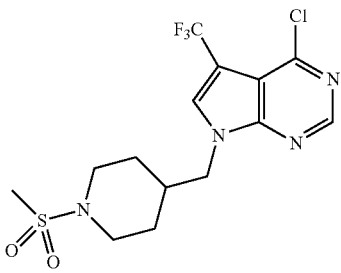

Into an 8 mL vial were added 4-chloro-7-(piperidin-4-ylmethyl)-5-(trifluoromethyl)-7H-pyrrolo[2,3-d]pyrimidine 2,2,2-trifluoroacetate (14.5 mg, 0.034 mmol), DCM (1 ml), methanesulfonyl chloride (3.92 µl, 0.050 mmol), and TEA (0.016 ml, 0.117 mmol). The solution was stirred at RT for 1 hr and then concentrated. The product was purified by Biotage flash chrom, 10 g SiO2, 0-100% EA/Hex. The title compound was obtained as a white solid (11.1 mg, 83%). MS (ESI): mass calcd. for $C_{14}H_{16}ClF_3N_4O_2S$, 396.06; m/z found, 397.3 [M+H]+; $^1$H NMR (500 MHz, CDCl$_3$) δ 8.75 (s, 1H), 7.09 (d, J=0.95 Hz, 1H), 4.31 (d, J=7.57 Hz, 2H), 3.76-3.88 (m, 2H), 2.77 (s, 3H), 2.60 (m, 2H), 2.16-2.27 (m, 1H), 1.61-1.64 (m, 2H), 1.52-1.56 (m, 2H).

Synthesis of 7-benzyl-5-(trifluoromethyl)-7H-pyrrolo[2,3-d]pyrimidin-4-amine

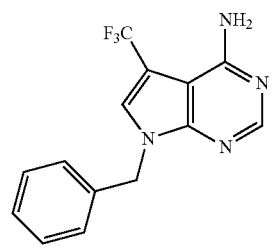 [SMILES: Nc1ncnc2c1c(C(F)(F)F)cn2Cc1ccccc1]

Into a 0.5-2 mL microwave vial were added 7-benzyl-4-chloro-5-(trifluoromethyl)-7H-pyrrolo[2,3-d]pyrimidine (9.0 mg, 0.029 mmol), dioxane (0.5 mL), and NH$_4$OH (aq) (1 ml, 0.029 mmol). The reaction was heated in the microwave at 150° C. for 1 hr. Evaporated the dioxane using a stream of N$_2$ and extracted with 3×2 mL EA. Combined organics, washed with 1 mL brine, dried with Na$_2$SO$_4$, filtered, concentrated. Filtered through a 2 g SiO$_2$ pad eluting with 30 mL EA, collecting four 7 mL fractions. Fractions 2-3 were combined and concentrated to afford the title compounds as a white solid (6.1 mg, 72%). MS (ESI): mass calcd. for $C_{14}H_{11}F_3N_4$, 292.09; m/z found, 293.2 [M+H]+; $^1$H NMR (500 MHz, CDCl$_3$) δ 8.44 (s, 1H), 7.28-7.25 (m, 3H), 7.13-7.12 (m, 2H), 6.87 (d, J=0.95 Hz, 1H), 5.55 (s, 2H), 5.26 (bs, 2H).

Synthesis of 2-amino-1-(3-methoxybenzyl)-4,5,6,7-tetrahydro-1H-indole-3-carbonitrile

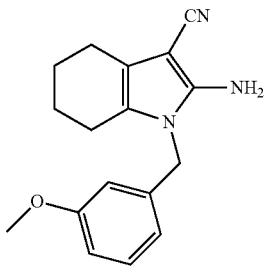 [SMILES: COc1cccc(Cn2c(N)c(C#N)c3c2CCCC3)c1]

Into a 40 mL vial were added 2-hydroxycyclohexanone (0.27 g, 2.365 mmol), Ts-OH (0.045 g, 0.237 mmol), 4 Å MS powder (1.05 g), cyclohexane (15 ml), and (3-methoxyphenyl)methanamine (0.303 ml, 2.365 mmol). The suspension was stirred at 80° C. for 1 hr. This was cooled to 50-60° C. and malononitrile (0.149 ml, 2.365 mmol) and piperidine (0.094 ml, 0.946 mmol) were added. The resulting mixture was stirred at 60° C. for 15 min and then cooled to RT. Concentrated the reaction to a dark residue. Resuspended the residue with 10 mL DCM. Filtered the suspension to remove most of the sieves. Centrifuged the filtrate and decanted to remove the remaining sieves. Concentrated the decanted solution to a dark oil. Purified by Biotage flash chrom, 25 g SiO2, eluting with 0-30% EA/Hex. Obtained the title compound as a tan solid (0.30 g, 45%). MS (ESI): mass calcd. for $C_{17}H_{19}N_4O$, 281.15; m/z found, 282.2 [M+H]+; $^1$H NMR (500 MHz, CDCl$_3$) δ 1.70-1.84 (m, 4H), 2.32-2.40 (m, 2H), 2.46-2.52 (m, 2H), 3.60 (br. s., 2H), 3.79 (s, 3H), 4.85 (s, 2H), 6.56 (d, J=2.21 Hz, 1H), 6.61 (dq, J=7.57, 0.84 Hz, 1H), 6.83 (dd, J=8.20, 2.21 Hz, 1H), 7.25-7.29 (m, 1H).

Synthesis of 9-(3-methoxybenzyl)-6,7,8,9-tetrahydro-5H-pyrimido[4,5-b]indol-4-ol

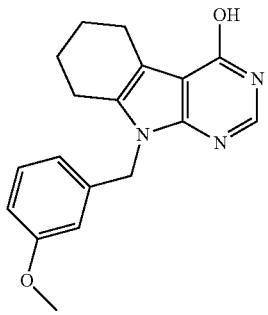 [SMILES: COc1cccc(Cn2c3c(c4c(O)ncnc42)CCCC3)c1]

Into a 2-5 mL microwave vial were added 2-amino-1-(3-methoxybenzyl)-4,5,6,7-tetrahydro-1H-indole-3-carbonitrile (0.28 g, 0.995 mmol) and formic acid (88%) (3 ml, 0.995 mmol). The solution was heated in a microwave at 120° C. for 2.5 hrs. The dark solution was added to 20 g of ice water. The solid was filtered, washed with water, and dried in a vacuum dessicator. The title compound was thus obtained as an off-white solid (129.1 mg, 42%). MS (ESI): mass calcd. for $C_{18}H_{19}N_3O$, 309.36; m/z found, 310.2 [M+H]+; $^1$H NMR (500 MHz, CDCl$_3$) 11.02 (bs, 1H), 7.81 (s, 1H), 7.19-7.24 (m, 1H), 6.79 (d, J=2.21 Hz, 1H), 6.65 (dd, J=0.63, 7.57 Hz, 1H), 6.60-6.63 (m, 1H), 5.27 (s, 2H), 3.75 (s, 3H), 2.91 (t, J=5.83 Hz, 2H), 2.50 (t, J=5.83 Hz, 2H), 1.73-1.87 (m, 4H).

Synthesis of 4-chloro-9-(3-methoxybenzyl)-6,7,8,9-tetrahydro-5H-pyrimido[4,5-b]indole

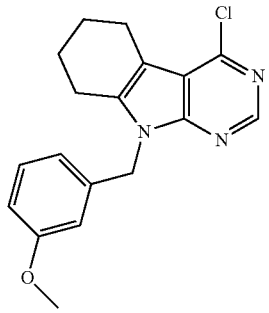

Into an 8 mL vial were added 9-(3-methoxybenzyl)-6,7,8,9-tetrahydro-5H-pyrimido[4,5-b]indol-4-ol (50.9 mg, 0.165 mmol) and phosphoryl trichloride (1 ml, 10.73 mmol). The suspension was heated at 80° C. for 1 hr, by which time it had become a dark red solution. The solution was concentrated and 2 mL of sat aq. NaHCO$_3$ was added. The suspension was stirred for 5 min until bubbling ceased. The product was extracted with 2×2 mL DCM, filtered through a phase separator, and concentrated. The residue was purified by Biotage flash chrom, eluting with 0-50% EA/Hex, 5 g SiO$_2$, to obtain the title compound as a tan solid (37.7 mg, 70%). MS (ESI): mass calcd. for $C_{18}H_{18}ClN_3O$, 327.81; m/z found, 328.2 [M+H]+; $^1$H NMR (500 MHz, CDCl$_3$) δ 8.53 (s, 1H), 7.20-7.22 (m, 1H), 6.77-6.81 (m, 1H), 6.63-6.64 (m, 2H), 5.37 (s, 2H), 3.74 (s, 3H), 2.93-2.94 (m, 2H), 2.59-2.61 (m, 2H), 1.84-1.86 (m, 4H).

Synthesis of tert-butyl 4-((4-methyl-5-(trifluoromethyl)-7H-pyrrolo[2,3-d]pyrimidin-7-yl)methyl)piperidine-1-carboxylate

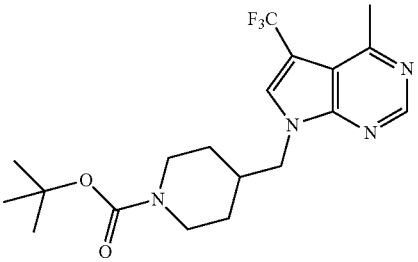 [SMILES: Cc1ncnc2c1c(C(F)(F)F)cn2CC1CCN(C(=O)OC(C)(C)C)CC1]

Into a 8 mL vial were added tert-butyl 4-((4-chloro-5-(trifluoromethyl)-7H-pyrrolo[2,3-d]pyrimidin-7-yl)methyl) piperidine-1-carboxylate (45 mg, 0.107 mmol) and THF (2 ml) and Pd(Ph$_3$P)$_4$ (24.83 mg, 0.021 mmol) and trimethylaluminum, 2.0 M in toluene (0.107 ml, 0.215 mmol). The mixture was heated at 65° C. for 15 min and then cooled to RT and added 2 mL sat. aq. NH$_4$Cl slowly and stirred until bubbling ceased. Evaporated the organics and extracted with 3×2 mL EA. Washed the combined organics with 2 mL brine and concentrated. Purified by Biotage flash chrom, 10 g SiO2, 20-100% EA/Hex. to afford the title compound as a brown oil. MS (ESI): mass calcd. for C₉H₂₅F₃N₄O₂, 398.42; m/z found, 399.4 [M+H]+; ¹H NMR (500 MHz, CDCl₃) δ 8.87 (s, 1H), 7.03 (s, 1H), 4.25 (d, J=7.57 Hz, 2H), 4.10-4.14 (m, 2H), 2.77 (s, 3H), 2.54-2.65 (m, 2H), 2.17-2.30 (m, 1H), 1.47-1.45 (m, 2H), 1.45 (s, 91), 1.31-1.27 (m, 2H).

Synthesis of 4-chloro-5-(trifluoromethyl)-7H-pyrrolo[2,3-d]pyrimidin-2-amine

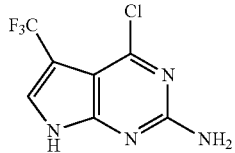

Into an 8 mL vial were added 4-chloro-7H-pyrrolo[2,3-d]pyrimidin-2-amine (50 mg, 0.297 mmol) and DCM (2.5 ml), sodium trifluoromethylsulfinate (139 mg, 0.890 mmol) and water (1.0 mL). The mixture was cooled to 0° C. To this was added tert-butyl hydroperoxide (0.205 ml, 1.483 mmol) dropwise and the resulting mixture was stirred at RT overnight. Added 3 mL of sat aq NaHCO₃. Separated layers and extracted aqueous with 2×2 mL DCM. Combined and concentrated organics. Purified by Biotage flash chrom, 10 g SiO2, eluting with 0-15% MeOH/DCM. Obtained the title compound as a yellow oil which was used as is. MS (ESI): mass calcd. for C₇H₄F₃N₄, 236.01; m/z found, 237.1 [M+H]+.

Synthesis of tert-butyl 4-((2-amino-4-chloro-5-(trifluoromethyl)-7H-pyrrolo[2,3-d]pyrimidin-7-yl) methyl)piperidine-1-carboxylate

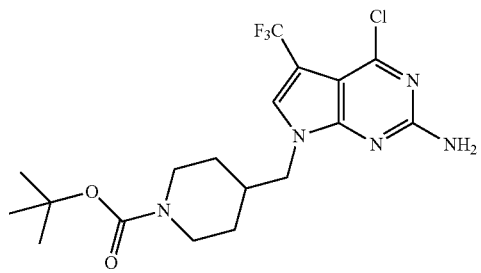 [SMILES: CC(C)(C)OC(=O)N1CCC(Cn2cc(C(F)(F)F)c3c(Cl)nc(N)nc32)CC1]

Into an 8 mL vial were added 4-chloro-5-(trifluoromethyl)-7H-pyrrolo[2,3-d]pyrimidin-2-amine (0.21 g, 0.888 mmol), K₂CO₃ (0.147 g, 1.065 mmol), DMF (2 mL), and tert-butyl 4-(bromomethyl)piperidine-1-carboxylate (0.247 g, 0.888 mmol). Stirred the suspension at 60 C for 6 hrs. Concentrated the reaction. Purified by Biotage flash chrom, 10 g SiO2, eluting with 0-30% EA/Hex. Fractions containing desired product were combined and concentrated and purified by prep HPLC. Sent the residue for prep HPLC purification (Phenomenex Gemini-NX, C18, 150×21.2 mm, 5 uM particle size, 110 A pore size. Mobile Phase A=0.1% Formic Acid in water, Mobile Phase B=0.1% Formic Acid in acetonitrile, eluted with 45% B-75% B gradient). Obtained the title compound as a white solid (63.4 mg, 16%). MS (ESI): mass calcd. for C₁₈H₂₃ClF₃N₅O₂, 433.86; m/z found, 434.25 [M+H]+; ¹H NMR (500 MHz, CDCl₃) 8.00 (s, 1H), 6.86 (d, J=0.95 Hz, 1H), 5.16 (br. s., 2H), 4.07-4.21 (m, 2H), 4.05 (d, J=7.57 Hz, 2H), 2.56-2.70 (m, 2H), 2.08-2.19 (m, 1H), 1.39-1.49 (m, 2H), 1.45 (s, 9H), 1.25-1.27 (m, 2H).

Synthesis of tert-butyl 4-((4-chloro-7H-pyrrolo[2,3-d]pyrimidin-7-yl)methyl)piperidine-1-carboxylate

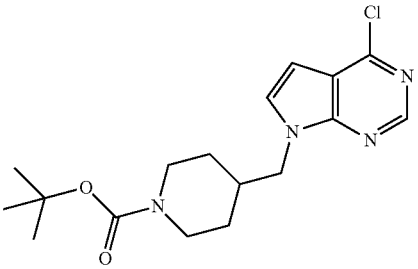 [SMILES: CC(C)(C)OC(=O)N1CCC(Cn2ccc3c(Cl)ncnc32)CC1]

Into an 40 mL vial were added 4-chloro-7H-pyrrolo[2,3-d]pyrimidine (0.10 g, 0.651 mmol), K₂CO₃ (0.108 g, 0.781 mmol), DMF (1 mL), and tert-butyl 4-(bromomethyl)piperidine-1-carboxylate (0.199 g, 0.716 mmol). Stirred the suspension at 60 C overnight. Concentrated rxn. Purified by Biotage flash chrom, 10 g SiO2, eluting with 0-50% EA/Hex to obtain the title compound as a colorless oil (0.17 g, 74%). MS (ESI): mass calcd. for C₁₇H₂₃ClN₄O₂, 350.84; m/z found, 351.34 [M+H]+; ¹H NMR (500 MHz, CDCl₃) δ 8.64 (s, 1H), 7.21 (d, J=3.47 Hz, 1H), 6.62 (d, J=3.47 Hz, 1H), 4.16 (d, J=7.25 Hz, 2H), 4.06-4.14 (m, 2H), 2.64 (t, J=12.61 Hz, 2H), 2.01-2.12 (m, 1H), 1.53 (d, J=12.61 Hz, 2H), 1.44 (s, 9H), 1.22 (dd, J=3.94, 12.45 Hz, 2H).

Synthesis of tert-butyl 4-((2,4-dichloro-7H-pyrrolo[2,3-d]pyrimidin-7-yl)methyl)piperidine-1-carboxylate

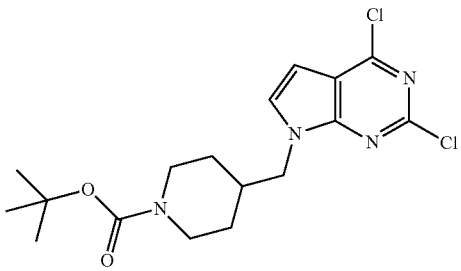 [SMILES: CC(C)(C)OC(=O)N1CCC(Cn2ccc3c(Cl)nc(Cl)nc32)CC1]

Into an 8 mL vial were added 2,4-dichloro-7H-pyrrolo[2,3-d]pyrimidine (0.20 g, 1.064 mmol), K₂CO₃ (0.176 g, 1.276 mmol), DMF (3 mL), and tert-butyl 4-(bromomethyl)piperidine-1-carboxylate (0.326 g, 1.170 mmol). Stirred the suspension at 60° C. for 5 hrs. Concentrated rxn. The residue was purified by Biotage flash chrom, 10 g SiO2, eluting with 0-30% EA/Hex. Combined and concentrated desired fractions to obtain the title compound as a yellow oil (83.3 mg, 20%). MS (ESI): mass calcd. for C₁₇H₂₂Cl₂N₄O₂, 385.29; m/z found, 385.20 [M+H]+; ¹H NMR (500 MHz, CDCl₃) δ 7.17 (d, J=3.78 Hz, 1H), 6.61 (d, J=3.47 Hz, 1H), 4.06-4.17 (m, 4H), 2.62-2.67 (m, 2H), 2.02-2.06 (m, 1H), 1.51-1.57 (m, 2H), 1.16-1.28 (m, 2H).

Synthesis of 4-bromo-7-((1-(methylsulfonyl)piperidin-4-yl)methyl)-5-(trifluoromethyl)-7H-pyrrolo[2,3-d]pyrimidine

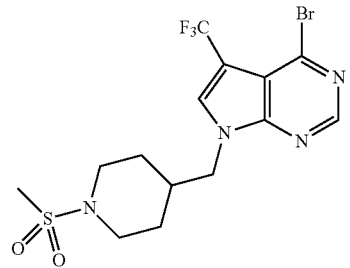

Into a 8 mL vial were added 4-chloro-7-((1-(methylsulfonyl)piperidin-4-yl)methyl)-5-(trifluoromethyl)-7H-pyrrolo[2,3-d]pyrimidine (25 mg, 0.063 mmol), TMS-Br (0.082 ml, 0.630 mmol), and acetonitrile (2 ml). The reaction was stirred at 40 C for 2 hrs and then RT for 3 days. Added 1 mL NaHCO$_3$ (sat., aq) and 2 mL ethyl acetate. Separated layers. Extracted aqueous with 2 mL EA. Combined organics, washed with 1 mL each water and brine. Dried over Na$_2$SO$_4$, filtered and concentrated. Triturated the off-white semi-solid with ether, sonicating to create a free-flowing solid. Filtered, washed with ether, dried. Obtained the title compound as a white solid (13.5 mg, 49%). MS (ESI): mass calcd. for C$_{14}$H$_{16}$BrF$_3$N$_4$O$_2$S, 441.27; m/z found, 443.05 [M+H]+; $^1$H NMR (500 MHz, CDCl$_3$) δ8.70 (s, 1H), 7.02 (d, J=0.63 Hz, 1H), 4.30 (d, J=7.88 Hz, 2H), 3.82 (d, J=11.98 Hz, 2H), 2.76 (s, 3H), 2.60 (d, J=2.52 Hz, 2H), 2.17-2.26 (m, 1H), 1.48-1.64 (m, 4H).

Synthesis of 4-fluoro-7-((1-(methylsulfonyl)piperidin-4-yl)methyl)-5-(trifluoromethyl)-7H-pyrrolo[2,3-d]pyrimidine

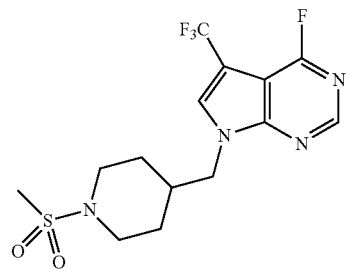 [SMILES: CS(=O)(=O)N1CCC(Cn2cc(C(F)(F)F)c3c(F)ncnc32)CC1]

Into a 0.5-2 mL microwave vial were added 4-chloro-7-((1-(methylsulfonyl)piperidin-4-yl)methyl)-5-(trifluoromethyl)-7H-pyrrolo[2,3-d]pyrimidine (25 mg, 0.063 mmol), KF (9.15 mg, 0.158 mmol), and DMSO (1 ml). The reaction was heated in the uW at 150 C for 1 hr. The rxn was concentrated. Purified by Biotage flash chrom, 10 g SiO2, eluting with 0~100% EA Hex to afford the title compound as a white solid (7.1 mg, 30%). MS (ESI): mass calcd. for C$_{14}$H$_{16}$F$_4$N$_4$O$_2$S, 380.36; m/z found, 381.16 [M+H]+; $^1$H NMR (500 MHz, CDCl$_3$) δ 8.65 (d, J=0.95 Hz, 1H), 7.08 (d, J=0.63 Hz, 1H), 4.33 (d, J=7.57 Hz, 2H), 3.83 (d, J=11.98 Hz, 2H), 2.79 (s, 3H), 2.61 (dt, J=2.68, 12.06 Hz, 2H), 2.14-2.28 (m, 1H), 1.46-1.68 (m, 4H).

Synthesis of tert-butyl 4-((4-chloro-5-methyl-7H-pyrrolo[2,3-d]pyrimidin-7-yl)methyl)piperidine-1-carboxylate

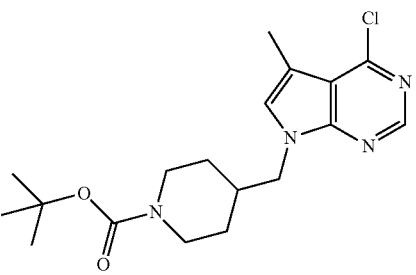 [SMILES: Cc1cn(CC2CCN(C(=O)OC(C)(C)C)CC2)c2ncnc(Cl)c12]

Into a 40 mL vial were added 4-chloro-5-methyl-7H-pyrrolo[2,3-d]pyrimidine (0.10 g, 0.597 mmol) and DMF (2 ml), tert-butyl 4-(bromomethyl)piperidine-1-carboxylate (0.199 g, 0.716 mmol) and Cs$_2$CO$_3$ (0.389 g, 1.193 mmol). The reaction was stirred at 60° C. for 1 hr RT overnight. Concentrated rxn. Purified by Biotage flash chrom, 25 g SiO2, eluting with 0-75% EA/Hex over. Combined and concentrated the one main peak that eluted to afford the title compounds as a light-yellow colored oil (0.19 g, 87%). MS (ESI): mass calcd. for C$_{18}$H$_{25}$ClN$_4$O$_2$, 364.87; m/z found, 365.36 [M+H]+; $^1$H NMR (500 MHz, CDCl$_3$) δ 8.56 (s, 1H), 6.94 (d, J=0.95 Hz, 1H), 4.08-4.14 (m, 4H), 2.57-2.69 (m, 2H), 2.01-2.04 (m, 1H), 1.48-1.57 (m, 2H), 1.44 (s, 9H), 1.12-1.29 (m, 2H).

Synthesis of 4-chloro-6-(trifluoromethyl)-7H-pyrrolo[2,3-d]pyrimidine

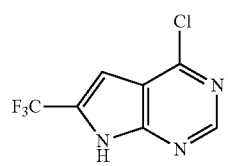 [SMILES: FC(F)(F)c1cc2c(Cl)ncnc2[nH]1]

Into a 500 mL 3-neck RBF were added 4-chloro-7H-pyrrolo[2,3-d]pyrimidine (8.04 g, 52.4 mmol) and DCM (150 ml), sodium trifluoromethylsulfinate (24.51 g, 157 mmol) and water (60.0 ml). The mixture was cooled to 0° C. To this was added tert-butyl hydroperoxide (36.2 ml, 262 mmol) dropwise over 45 min and the resulting mixture was stirred at RT for 3 days. A volume of (10 mL of sat aq. NaHCO$_3$ was slowly added to minimize foaming and stirred for 10 min. The layers were separated and the aqueous was extracted with 3×50 mL DCM. The organics were combined, washed with water and brine, dried with Na2SO4, filtered, and concentrated. The residue was purified by Biotage flash chrom, 100 g SiO2, eluting with 0-50% EA/Hex. Isolated the title compound as a tan-colored solid. $^1$H NMR (500 MHz, CDCl$_3$) δ 11.03 (bs, 1H), 8.77 (s, 1H), 7.82 (s, 1H).

Synthesis of tert-butyl 4-((4-chloro-6-(trifluoromethyl)-7H-pyrrolo[2,3-d]pyrimidin-7-yl)methyl)piperidine-1-carboxylate

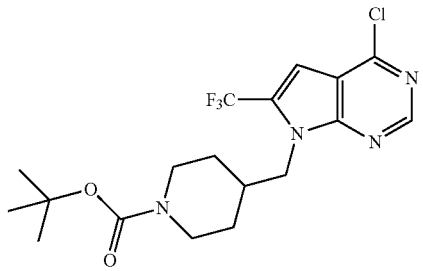 [SMILES: CC(C)(C)OC(=O)N1CCC(Cn2c(C(F)(F)F)cc3c(Cl)ncnc32)CC1]

Into a 8 mL vial were added 4-chloro-6-(trifluoromethyl)-7H-pyrrolo[2,3-d]pyrimidine (52 mg, 0.235 mmol), DMF (2 ml), Cs2CO3 (115 mg, 0.352 mmol), tert-butyl 4-(bromomethyl)piperidine-1-carboxylate (78 mg, 0.282 mmol) and the suspension was stirred at 50° C. overnight. Concentrated rxn. The residue was purified by Biotage flash chrom, 10 g SiO2, 0-50% EA/Hex to afford the title compound as a colorless oil. MS (ESI): mass calcd. for $C_{18}H_{22}ClF_3N_4O_2$, 418.84; m/z found, 419.34 [M+H]+; $^1$H NMR (500 MHz, CDCl$_3$) δ 1.17-1.31 (m, 2H), 1.45 (s, 9H), 1.55-1.59 (m, 2H), 2.07-2.13 (m, 1H), 2.64-2.69 (m, 2H), 4.11-4.15 (m, 2H), 4.21 (d, J=7.25 Hz, 2H), 7.62 (s, 1H), 8.74 (s, 1H).

Synthesis of 7-((1-(methylsulfonyl)piperidin-4-yl)methyl)-5-(trifluoromethyl)-7H-pyrrolo[2,3-d]pyrimidin-4-ol

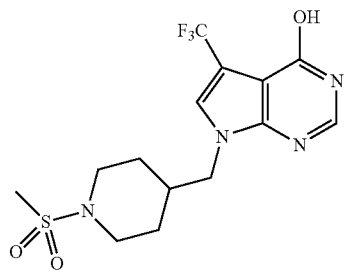 [SMILES: CS(=O)(=O)N1CCC(Cn2cc(C(F)(F)F)c3c(O)ncnc32)CC1]

Into an 4 mL vial were added 4-chloro-7-((1-(methylsulfonyl)piperidin-4-yl)methyl)-5-(trifluoromethyl)-7H-pyrrolo[2,3-d]pyrimidine (7.8 mg, 0.020 mmol), 1N HCl (1 mL), THF (1 mL), and the solution was stirred at 40 C for 4 hrs and RT overnight. Concentrated rxn. Added 2 mL DCM and washed with sat. aq. NaHCO3, brine, and dried with Na$_2$SO$_4$, filtered, and concentrated. Triturated with ether to afford the title compound as a white solid (4.1 mg, 55%). MS (ESI): mass calcd. for $C_{14}H_{17}F_3N_4O_3S$, 378.37; m/z found, 379.18 [M+H]+; $^1$H NMR (500 MHz, CDCl$_3$) δ 10.02-10.46 (bs, 1H), 7.95 (s, 1H), 7.17 (s, 1H), 4.22 (d, J=7.63 Hz, 2H), 3.77-3.89 (m, 2H), 2.78 (s, 3H), 2.56-2.67 (m, 2H), 2.04-2.17 (m, 1H), 1.62-1.69 (m, 1H), 1.47-1.53 (m, 1H).

Synthesis of 4-bromo-7-(piperidin-4-ylmethyl)-5-(trifluoromethyl)-7H-pyrrolo[2,3-d]pyrimidin-2-amine

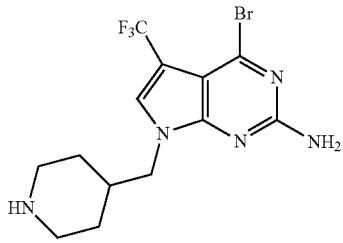 [SMILES: Nc1nc(Br)c2c(C(F)(F)F)cn(CC3CCNCC3)c2n1]

Into a 8 mL vial were added ten-butyl 4-((2-amino-4-chloro-5-(trifluoromethyl)-7H-pyrrolo[2,3-d]pyrimidin-7-yl)methyl)piperidine-1-carboxylate (15 mg, 0.035 mmol), TMS-Br (0.045 ml, 0.346 mmol), and acetonitrile (2 ml). The reaction was stirred at 40 C for 1 hr and then RT for 3 days. Added 1 mL NaHCO$_3$ (sat., aq) and 2 mL, EA. Separated layers. Extracted aqueous with 2 mL EA. Combined organics, washed with 1 mL each water and brine. Dried over Na$_2$SO$_4$, filtered and concentrated. Triturated the off-white semi-solid with ether, sonicating to create a free-flowing solid. Filtered, washed with ether, dried. Obtained the title compound as a white solid (5.1 mg, 39%). MS (ESI): mass calcd. for $C_{13}H_{15}BrF_3N_5$, 378.18; m/z found, 380.21 [M+H]+; $^1$H NMR (500 MHz, DMSO-d$_6$) δ 1.36-1.43 (m, 2H), 1.58-1.61 (m, 2H), 2.14-2.25 (m, 1H), 2.78-2.85 (m, 2H), 3.24-3.27 (m, 2H), 3.98-4.04 (m, 2H), 6.94 (s, 1H), 7.12, (bs, 11H), 8.19 (bs, 1H), 8.50 (bs, 1H).

Synthesis of tert-butyl 4-((2-amino-4-chloro-7H-pyrrolo[2,3-d]pyrimidin-7-yl)methyl)piperidine-1-carboxylate

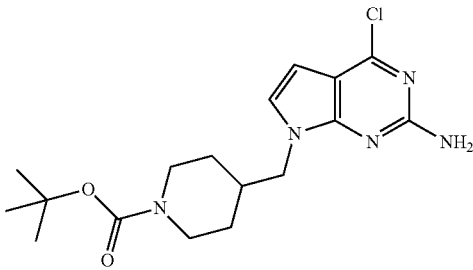 [SMILES: CC(C)(C)OC(=O)N1CCC(Cn2ccc3c(Cl)nc(N)nc32)CC1]

Into an 8 mL vial were added 4-chloro-7H-pyrrolo[2,3-d]pyrimidin-2-amine (0.10 g, 0.593 mmol), K$_2$CO$_3$ (0.098 g, 0.712 mmol), DMF (2 mL), and tert-butyl 4-(bromomethyl)piperidine-1-carboxylate (0.182 g, 0.652 mmol). Stirred the suspension at 80 C for 3 days. Added an additional 2 eq of bromide and 2.5 eq of K$_2$CO, stirred at 100 C overnight. Purified by Biotage flash chrom, 10 g SiO2, eluting with 0-40% EA/Hex. Obtained the title compound as a yellow oil (92 mg, 42%). MS (ESI): mass calcd. for $C_1H_{24}ClN_5O_2$, 365.86; m/z found, 366.27 [M+H]+; 1H NMR (500 MHz, CDCl$_3$) δ 8.02 (s, 1H), 6.82 (d, J=3.47 Hz, 1H), 6.40 (d, J=3.47 Hz, 1H), 5.00-5.14 (m, 1H), 4.12 (bs, 1H), 3.95 (d, J=7.25 Hz, 2H), 2.56-2.73 (m, 2H), 1.95-2.03 (m, 1H), 1.54 (br. s., 2H), 1.44 (s, 9H)), 1.16-1.27 (m, 2H).

Synthesis of 4-bromo-7-(piperidin-4-ylmethyl)-7H-pyrrolo[2,3-d]pyrimidin-2-amine

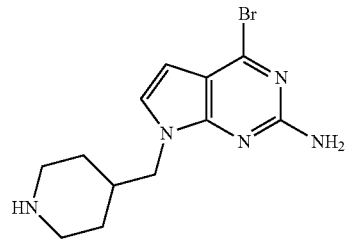 [SMILES: Nc1nc(Br)c2ccn(CC3CCNCC3)c2n1]

Into a 8 mL vial were added tert-butyl 4-((2-amino-4-chloro-7H-pyrrolo[2,3-d]pyrimidin-7-yl)methyl)piperidine-1-carboxylate (25 mg, 0.068 mmol), TMS-Br (0.089 ml, 0.683 mmol), and acetonitrile (Volume: 2 ml). The reaction was stirred at 40 C for 1 hr and then RT for 3 days. Added 1 mL NaHCO3 (aq) and 2 mL EA. Separated layers. Extracted aqueous with 2 mL EA. Combined organics, washed with 1 mL each water and brine. Dried over $Na_2SO_4$, filtered and concentrated. Triturated the off-white semi-solid with ether, sonicating to create a free-flowing solid. Filtered, washed with ether, dried. Obtained the title compound as a white solid (14.4 mg, 68%). MS (ESI): mass calcd. for $C_{11}H_{16}BrN_5$, 310.19; m/z found, 312.22 [M+H]+; $^1$H NMR (500 MHz, CDCl$_3$) δ 1.27-1.42 (m, 2H), 1.60 (d, J=13.12 Hz, 10H), 2.01-2.14 (m, 1H), 2.72-2.88 (m, 2H), 3.25 (d, J=12.51 Hz, 2H), 3.95 (m, 2H), 6.22 (d, J=3.66 Hz, 1H), 7.18 (d, J=3.66 Hz, 2H), 8.25 (d, J=10.07 Hz, 1H), 8.55 (d, J=9.46 Hz, 1H); $^{13}$C NMR (125 MHz, CDCl$_3$) δ 158.86, 152.44, 143.45, 126.87, 111.73, 99.62, 48.37, 42.69, 33.94, 26.02.

Exemplary compounds synthesized by the disclosed methods are listed in Table 1 below and Table 2 presented in Example 2 below.

TABLE 1-continued

| Compound ID | Structure |
|---|---|
| NUCC-0077073 | (structure) |
| NUCC-0077072 | (structure) |
| NUCC-0077071 | (structure) |
| NUCC-0077070 | (structure) |
| NUCC-0077069 | (structure) |
| NUCC-0054150 | (structure) |
| NUCC-0054044 | (structure) |
| NUCC-0000597 | (structure) |
| NUCC-0000594 | (structure) |

TABLE 1-continued
| Compound ID | Structure |
|---|---|
| NUCC-0000573 | 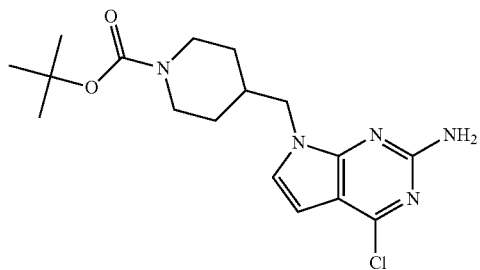 [SMILES: CC(C)(C)OC(=O)N1CCC(Cn2ccc3c(Cl)nc(N)nc32)CC1] |
| NUCC-0000572 | 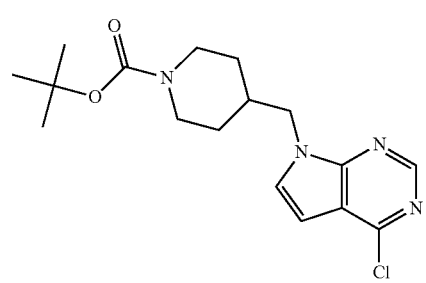 [SMILES: CC(C)(C)OC(=O)N1CCC(Cn2ccc3c(Cl)ncnc32)CC1] |
| NUCC-0000569 | 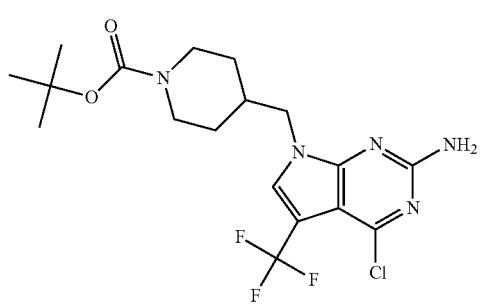 |
| NUCC-0000510 | 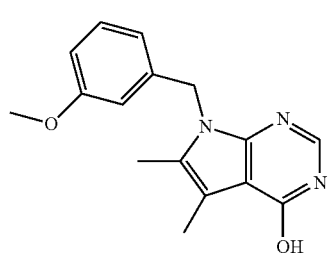 [SMILES: COc1cccc(Cn2c(C)c(C)c3c(O)ncnc32)c1] |
| NUCC-0000509 | 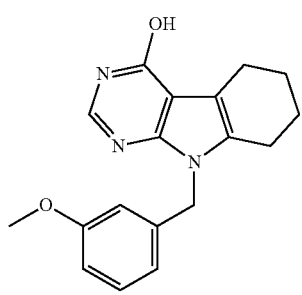 [SMILES: COc1cccc(Cn2c3c(c4c(O)ncnc42)CCCC3)c1] |
| NUCC-0000508 | 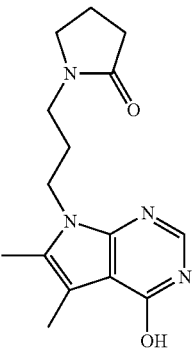 [SMILES: Cc1c(C)n(CCCN2CCCC2=O)c2ncnc(O)c12] |
| NUCC-0000507 | 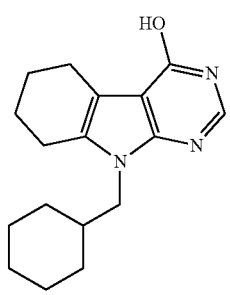 [SMILES: Oc1ncnc2c1c1c(n2CC2CCCCC2)CCCC1] |
| NUCC-0000506 | 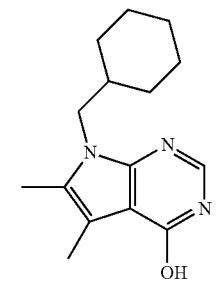 [SMILES: Cc1c(C)n(CC2CCCCC2)c2ncnc(O)c12] |
| NUCC-0000505 | 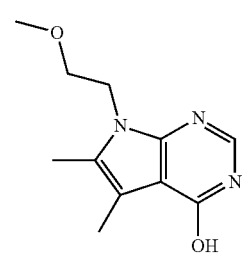 [SMILES: COCCn1c(C)c(C)c2c(O)ncnc21] |
| NUCC-0000504 | 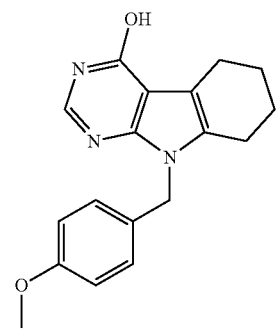 [SMILES: COc1ccc(Cn2c3c(c4c(O)ncnc42)CCCC3)cc1] |

TABLE 1-continued

| Compound ID | Structure |
|---|---|
| NUCC-0000503 | (structure) |
| NUCC-0000502 | (structure) |
| NUCC-0000476 | (structure) |
| NUCC-0000414 | (structure) |
| NUCC-0000411 | (structure) |
| NUCC-0000410 | (structure) |
| NUCC-0000402 | (structure) |
| NUCC-0000401 | (structure) |

TABLE 1-continued

| Compound ID | Structure |
|---|---|
| NUCC-0000385 | (7-(4-fluorobenzyl)-5,6-dimethyl-4-fluoro-7H-pyrrolo[2,3-d]pyrimidine) |
| NUCC-0000384 | (1-acetyl-4-((4-chloro-5-(trifluoromethyl)-7H-pyrrolo[2,3-d]pyrimidin-7-yl)methyl)piperidine) |
| NUCC-0000382 | (7-(4-fluorobenzyl)-4-methoxy-5,6-dimethyl-7H-pyrrolo[2,3-d]pyrimidine) |
| NUCC-0000380 | (4-chloro-7-((4-methoxyphenyl)sulfonyl)-5-(trifluoromethyl)-7H-pyrrolo[2,3-d]pyrimidine) |
| NUCC-0000379 | (tert-butyl 4-((4-amino-5-(trifluoromethyl)-7H-pyrrolo[2,3-d]pyrimidin-7-yl)methyl)piperidine-1-carboxylate) |
| NUCC-0000378 | (4-chloro-5,6-dimethyl-7-(2-(pyrrolidin-1-yl)ethyl)-7H-pyrrolo[2,3-d]pyrimidine) |
| NUCC-0000377 | (4-chloro-5,6-dimethyl-7-(pyridin-3-ylmethyl)-7H-pyrrolo[2,3-d]pyrimidine) |
| NUCC-0000376 | (7-(2-methoxyethyl)-5,6-dimethyl-7H-pyrrolo[2,3-d]pyrimidin-4-amine) |
| NUCC-0000374 | (7-(cyclohexylmethyl)-5,6-dimethyl-7H-pyrrolo[2,3-d]pyrimidin-4-amine) |

TABLE 1-continued

| Compound ID | Structure |
|---|---|
| NUCC-0000373 | (structure) |
| NUCC-0000372 | (structure) |
| NUCC-0000371 | (structure) |
| NUCC-0000355 | (structure) |
| NUCC-0000354 | (structure) |
| NUCC-0000330 | (structure) |
| NUCC-0000328 | (structure) |
| NUCC-0000317 | (structure) |
| NUCC-0000316 | (structure) |
| NUCC-0000314 | (structure) |
| NUCC-0000307 | (structure) |

TABLE 1-continued

| Compound ID | Structure |
|---|---|
| NUCC-0000281 | (4-hydroxy-9-benzyl-6,7,8,9-tetrahydro-5H-pyrimido[4,5-b]indole structure) |

Example 2

Inhibition of MM.1S Cells by Substituted Pyrrolo[2,3-d]Pyrimidine Compounds

Summary

The substituted pyrrolo[2,3-d]pyrimidines disclosed herein are effective at reducing the proliferation of a number of cancer cell lines including MM.1S cancer cells, which are a multiple myeloma-derived cell line. MM.1 S is a multiple myeloma-derived cell line and therefore compounds that are cytotoxic against these cells have potential for treating this and other cancer types. Common structural features of the substituted pyrrolo[2,3-d]pyrimidines typically include a chlorine substitution at the 4-position. The 5- and 6-positions of the fused heterocyclic ring may be substituted on one or both of the carbons. For example, the 5- and 6-positions can each independently be small alkyl groups or joined to form a tricyclic 6,7,8,9-tetrahydro-5H-pyrimido[4,5-b]indole core system. When mono-substituted, a trifluoromethyl group at the 5-position provides particularly potent compounds. The N7 can be substituted with a wide variety of groups, including functionalized benzyl groups and heterocycles. The present compounds are shown to inhibit cell proliferation of multiple myeloma MM.1 S cells using the well-validated MTS cell proliferation assay. A number of the tested compounds have an $IC_{50}$ of 10 uM or lower in the MM.1 S MTS assay. Several compounds have an $IC_{50}$ of less than 1 uM.

Experimental

MM.1 S cells were treated with test compounds including NUCC-000381, NUCC-00383, NUCC-000501, NUCC-000482, and 8-amino adenosine, having the following formulas, respectively:

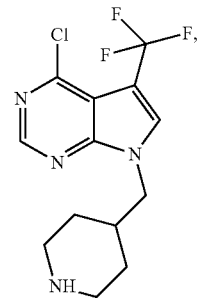

NUCC-000381

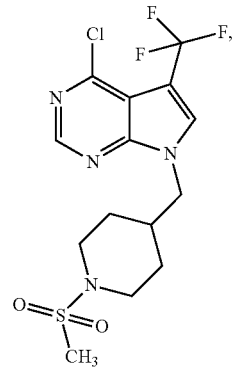

NUCC-000383

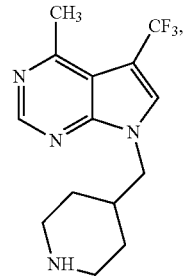

NUCC-000501

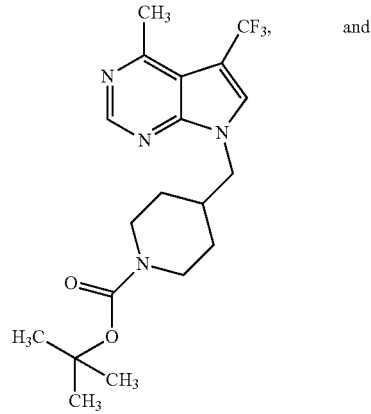

NUCC-000482 and

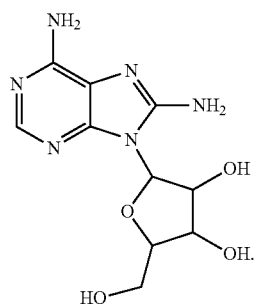

8-amino-adenosine

As shown in FIG. 1, the compounds were administered at concentrations ranging from 0.1 µM, 0.3 µM, 1 µM, 3 µM, and 10 µM. Cell viability was assessed by MTS assay as follows.

MTS Cell Titer 96 Assay.

The MTS CellTiter 96 assay is a colorimetric method to assess the number of viable cells based on the conversion of a tetrazolium compound (MTS) to a formazan product by the mitochondrial dehydrogenase enzyme of the cells. This assay is used to determine the number of viable cells remaining following a drug treatment in comparison to the number of viable cells that are only treated with the drug vehicle (control cells). The amount of formazan product in the control cells is normalized to 100% and the amount of formazan in the drug treated cells is expressed as a percentage of control. This is used to generate dose response curve and estimate the drug concentration that produced a 50% decrease in the number of viable cells.

Results.

NUCC-00381 and NUCC-000383 were each as effective in decreasing cell proliferation as 8-amine-adenosine, a compound under development for therapeutic application. In contrast, NUCC-000501 and NUCC-000482 were not effective in decreasing cell proliferation. Notably, NUCC-000501 and NUCC-000482 differ structurally from NUCC-00381 and NUCC-000383 based on the presence of a 4-methyl substituent rather than a 4-chloro substituent. Additional compounds that were synthesized and tested in the multiple myeloma MM.1 S/MTS cell proliferation assay are disclosed in Tables 2-14.

TABLE 2

| Compound ID | Structure | Estimated IC50 (µm) |
|---|---|---|
| NUCC-0000381 | (structure) | 0.6 |
| NUCC-0000383 | (structure) | 0.9 |
| NUCC-0000357 | (structure) | 1.5 |
| NUCC-0000383 | (structure) | 1.5 |
| NUCC-0000409 | (structure) | 1.5 |

TABLE 2-continued
| Compound ID | Structure | Estimated IC50 (μm) |
|---|---|---|
| NUCC-0000412 | 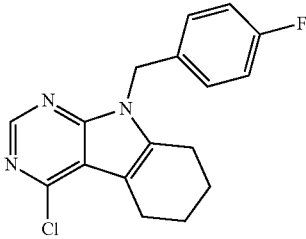 [SMILES: Fc1ccc(Cn2c3c(c4c(Cl)ncnc42)CCCC3)cc1] | 2.5 |
| NUCC-0000315 | 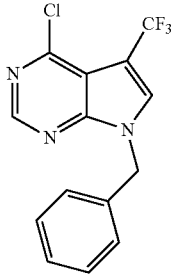 | 3 |
| NUCC-0000326 | 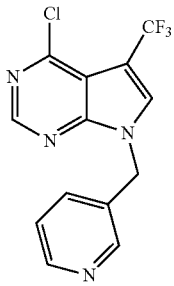 [SMILES: FC(F)(F)c1cn(Cc2cccnc2)c2ncnc(Cl)c12] | 3 |
| NUCC-0000576 | 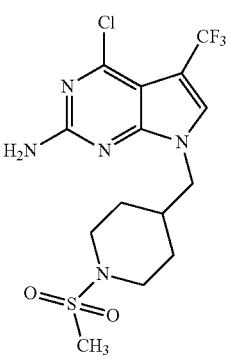 [SMILES: CS(=O)(=O)N1CCC(Cn2cc(C(F)(F)F)c3c(Cl)nc(N)nc32)CC1] | 3 |
| NUCC-0000575 | 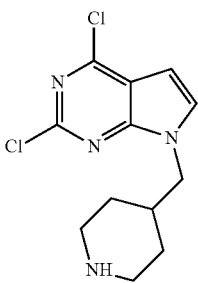 [SMILES: Clc1nc(Cl)c2ccn(CC3CCNCC3)c2n1] | 3 |
| NUCC-0000577 | 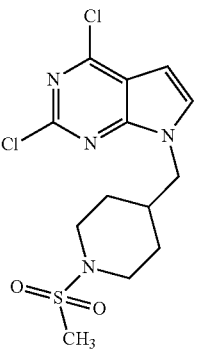 [SMILES: CS(=O)(=O)N1CCC(Cn2ccc3c(Cl)nc(Cl)nc32)CC1] | 5 |
| NUCC-0000571 | 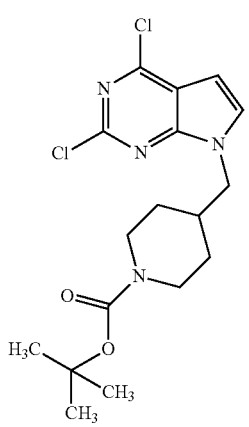 [SMILES: CC(C)(C)OC(=O)N1CCC(Cn2ccc3c(Cl)nc(Cl)nc32)CC1] | 5 |
| NUCC-0000329 | 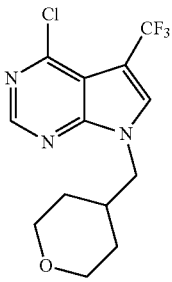 [SMILES: FC(F)(F)c1cn(CC2CCOCC2)c2ncnc(Cl)c12] | 3 |
| NUCC-0000358 | 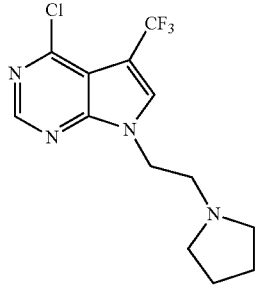 [SMILES: FC(F)(F)c1cn(CCN2CCCC2)c2ncnc(Cl)c12] | 3 |

TABLE 2-continued

| Compound ID | Structure | Estimated IC50 (μm) |
|---|---|---|
| NUCC-0000280 | 4-chloro-5,6-dimethyl-7-benzyl-7H-pyrrolo[2,3-d]pyrimidine | 5 |
| NUCC-0000325 | 4-chloro-5-trifluoromethyl-7-(4-fluorobenzyl)-7H-pyrrolo[2,3-d]pyrimidine | 5 |
| NUCC-0000327 | 4-chloro-5-trifluoromethyl-7-(pyridin-4-ylmethyl)-7H-pyrrolo[2,3-d]pyrimidine | 5 |
| NUCC-0000413 | 4-chloro-5,6-dimethyl-7-(2-morpholinoethyl)-7H-pyrrolo[2,3-d]pyrimidine | 5 |
| NUCC-0000360 | 4-chloro-5,6-dimethyl-7-(4-fluorobenzyl)-7H-pyrrolo[2,3-d]pyrimidine | 7 |
| NUCC-0000477 | 4,6-dimethyl-7-(β-D-ribofuranosyl)-7H-pyrrolo[2,3-d]pyrimidine | 8 |
| NUCC-0000598 | 4-bromo-5-trifluoromethyl-7-((1-methanesulfonylpiperidin-4-yl)methyl)-7H-pyrrolo[2,3-d]pyrimidine | 2 |
| NUCC-0000570 | 2-amino-4-chloro-5-trifluoromethyl-7-(piperidin-4-ylmethyl)-7H-pyrrolo[2,3-d]pyrimidine | 3 |
| NUCC-0000501 | 4-methyl-5-trifluoromethyl-7-(piperidin-4-ylmethyl)-7H-pyrrolo[2,3-d]pyrimidine | Inactive |

TABLE 2-continued

| Compound ID | Structure | Estimated IC50 (μm) |
|---|---|---|
| NUCC-0000482 | 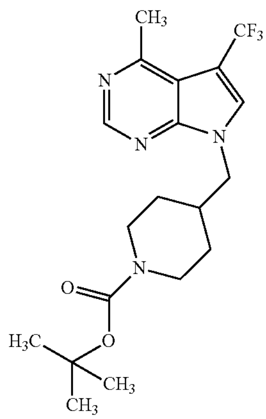 [SMILES: Cc1ncnc2c1c(C(F)(F)F)cn2CC1CCN(C(=O)OC(C)(C)C)CC1] | Inactive |
| NUCC-0000308 | 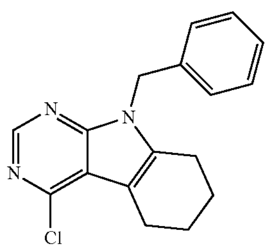 [SMILES: Clc1ncnc2c1c1c(n2Cc2ccccc2)CCCC1] | 10 |
| NUCC-0000359 | 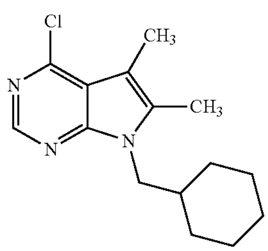 [SMILES: Cc1c(C)n(CC2CCCCC2)c2ncnc(Cl)c12] | 10 |
| NUCC-0000361 | 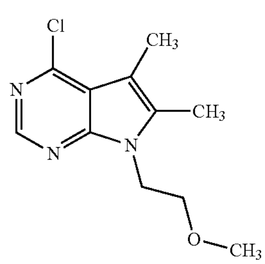 [SMILES: COCCn1c(C)c(C)c2c(Cl)ncnc21] | 10 |
| NUCC-0000362 | 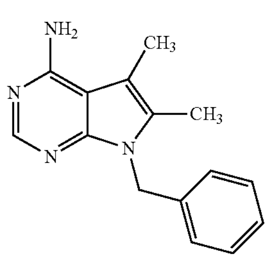 [SMILES: Cc1c(C)n(Cc2ccccc2)c2ncnc(N)c12] | 10 |
| NUCC-0000363 | | 10 |
| NUCC-0000375 | | 10 |
| NUCC-0000469 | | 10 |
| NUCC-0000470 | | 10 |
| NUCC-0000595 | | 3 |

TABLE 2-continued
| Compound ID | Structure | Estimated IC50 (μm) |
|---|---|---|
| NUCC-0000593 | 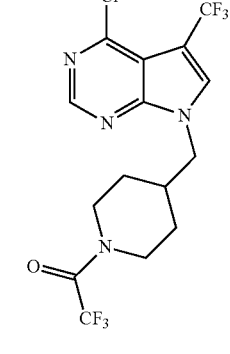 | 5 |
| NUCC-0000578 | | 5 |
| NUCC-0054043 | | 7 |
| NUCC-0054042 | | 0.3 |
| NUCC-0054041 | 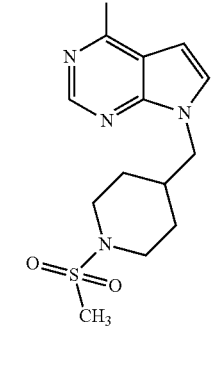 | 0.3 |
| NUCC-0054038 | 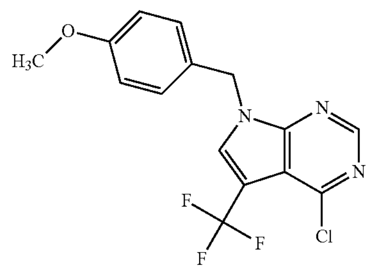 [SMILES: COc1ccc(Cn2cc(C(F)(F)F)c3c(Cl)ncnc32)cc1] | 2 |
| NUCC-0054037 | 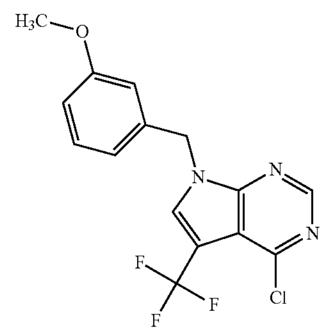 [SMILES: COc1cccc(Cn2cc(C(F)(F)F)c3c(Cl)ncnc32)c1] | 2 |
| NUCC-0050715 | 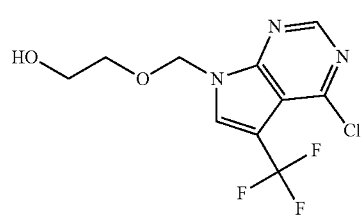 [SMILES: OCCOCn1cc(C(F)(F)F)c2c(Cl)ncnc21] | 5 |
| NUCC-0054151 | 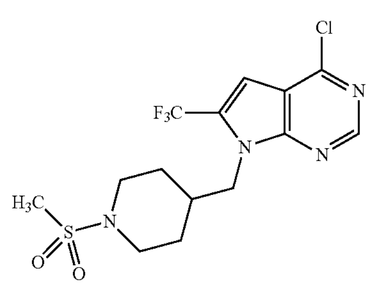 [SMILES: CS(=O)(=O)N1CCC(Cn2c(C(F)(F)F)cc3c(Cl)ncnc32)CC1] | >10 |

TABLE 2-continued

| Compound ID | Structure | Estimated IC50 (μm) |
|---|---|---|
| NUCC-0054150 | [structure: 4-chloro-6-(trifluoromethyl)-7-(piperidin-4-ylmethyl)-7H-pyrrolo[2,3-d]pyrimidine] | >10 |
| NUCC-0054040 | [structure: 4-chloro-5-methyl-7-((1-(methylsulfonyl)piperidin-4-yl)methyl)-7H-pyrrolo[2,3-d]pyrimidine] | 3 |
| NUCC-0054039 | [structure: 4-chloro-5-methyl-7-(piperidin-4-ylmethyl)-7H-pyrrolo[2,3-d]pyrimidine] | 1 |
| NUCC-0054036 | [structure: tert-butyl 4-((4-chloro-5-methyl-7H-pyrrolo[2,3-d]pyrimidin-7-yl)methyl)piperidine-1-carboxylate] | 2 |

Example 3

Evaluation of NUCL 381-3 and NUCL 383-3 for Inhibiting Growth of NCI-60 Cell Lines Summary.

NUCL 381-3 and NUCL 383-3 (referred to as "NUCC-00381" and "NUCC-000383" above, respectively) were administered to a variety of cancer cell lines in order to test their ability to inhibit cell growth as compared to doxorubicin. NUCL 381-3 and NUCL 383-3 were found to reduce cell viability for a number of cell lines and in some instances, they exhibited an activity similar to or better than that of doxorubicin.

Experimental

Cell Lines.

Tested cell lines included, Leukemia: CCRF-CEM, HL-60(TB), MOLT-4, RPMI-8226 and SR; Non-Small Cell Lung: A549/ATCC, EKVX, HOP-62, HOP-92, NCI-H226, NCI-H23, NCI-H322M, NCI-H460 and NCI-H522; Colon: COLO 205, HCC-2998, HCT-116, HCT-15. HT29, KM12 and SW-620; CNS: SF-268, SF-295, SF-539, SNB-19, SNB-75 and U251; Melanoma: LOX IMVI, MALME-3M, M14, MDA-MB-435, SK-MEL-2, SK-MEL-28, SK-MEL-5, UACC-257 and UACC-62; Ovarian: IGR-OV1, OVCAR-3, OVCAR-4, OVCAR-5, OVCAR-8. NCI/ADR-RES and SK-OV-3; Renal: 786-0, A498, ACHN, CAKI-1, RXF 393, SN12C, TK-10 and UO-31; Prostate: DU-145 and PC-3; and Breast: MCF7, MDA-MB-231/ATCC, MDA-MB-468, HS 578T, BT-549 and T-47D.

Media.

The cells were cultured in RPMI1640 media supplemented with 10% Fetal Bovine Serum (FBS), 2 mM glutamine and with 5% $CO_2$ and 37° C. For experiment, 5% of FBS and 50 ug/mL of gentamycin were used. Test articles were 10 μM of NUCL 381-3 or 10 μM NUCL 383-3. The positive control was 10 μM of doxorubicin.

Study.

Cells were plated in 96 well plates. The cells were plated in triplicate. Cells were plated at the densities based on NCI recommendation. Time zero cells (Tz) were fixed the following day with 50% or 80% ice cold Trichloracetic acid (TCA) and washed 5× with water. At 48 hours post addition of treatments, all remaining plates were fixed in 80% ice cold Trichloracetic acid (TCA) and washed 5× with water. After drying, one hundred microliters of 0.4% Sulphorhodamine B (SRB) in 1% acetic acid was added to each plate including the Tzero plate and incubated for 10 minutes at room temperature. After 5 additional washes with 1% acetic acid, plates were allowed to dry. One hundred microliters of Trizma base was added to each well and plates were read at 515 nm.

Calculations.

Percent of growth was calculated by the following formulas: [Ti/C]×100, where: Tz=absorbance readings for wells at time zero without treatment; C=absorbance readings of untreated cells (without treatment); and Ti=absorbance reading of wells with treatment. Results are presented in Table 3 and in FIGS. 2-10.

TABLE 3

| | | Percent viability | | |
|---|---|---|---|---|
| Cell Line Name | Type of cell | NUCL 381-3 | NUCL 383-3 | Doxorubicin |
| CCRF-CEM | Leukemia | 52.77 | 54.00 | 43.56 |
| HL-60(TB) | Leukemia | 25.78 | 22.46 | 24.97 |
| K-562 | Leukemia | 8.38 | 10.15 | 17.10 |
| MOLT-4 | Leukemia | 75.54 | 17.91 | 30.38 |
| RPMI-8226 | Leukemia | 100.00 | 100.00 | 44.22 |
| SR | Leukemia | 16.70 | 36.98 | 11.13 |
| A549 | Non-Small Cell Lung | 28.25 | 100.00 | 86.80 |
| EKVX | Non-Small Cell Lung | 57.45 | 84.58 | 35.55 |
| HOP-62 | Non-Small Cell Lung | 15.67 | 88.48 | 19.66 |
| HOP-92 | Non-Small Cell Lung | 56.76 | 97.57 | 98.52 |
| NCI-H226 | Non-Small Cell Lung | 54.88 | 29.52 | 34.20 |
| NCI-H23 | Non-Small Cell Lung | 42.34 | 46.10 | 27.56 |
| NCI-H322M | Non-Small Cell Lung | 68.09 | 53.75 | 42.58 |
| NCI-H460 | Non-Small Cell Lung | 26.36 | 69.10 | 35.01 |
| NCI-H522 | Non-Small Cell Lung | 38.73 | 21.70 | 18.15 |
| COLO 205 | Colon | 79.55 | 92.96 | 2.33 |
| HCC-2998 | Colon | 93.49 | 73.20 | 20.91 |
| HCT-116 | Colon | 20.12 | 15.03 | 14.91 |
| HCT-15 | Colon | 40.38 | 38.78 | 31.06 |
| HT29 | Colon | 33.33 | 30.28 | 34.92 |
| KM12 | Colon | 30.97 | 99.47 | 71.76 |
| SW-620 | Colon | 27.25 | 25.66 | 18.98 |

TABLE 3-continued

| Cell Line Name | Type of cell | Percent viability | | |
|---|---|---|---|---|
| | | NUCL 381-3 | NUCL 383-3 | Doxorubicin |
| SF-268 | CNS | 3.37 | 1.77 | 6.91 |
| SF-295 | CNS | 44.41 | 56.17 | 11.16 |
| SF-539 | CNS | 7.40 | 4.93 | 6.83 |
| SNB-19 | CNS | 28.89 | 21.40 | 37.30 |
| SNB-75 | CNS | 83.26 | 23.34 | 36.00 |
| U251 | CNS | 15.06 | 2.47 | 22.00 |
| LOX IMVI | Melanoma | 26.02 | 35.77 | 24.39 |
| MALME-3M | Melanoma | 100.69 | 42.69 | 15.75 |
| M14 | Melanoma | 96.17 | 78.51 | 25.47 |
| MDA-MB-435 | Melanoma | 65.54 | 46.59 | 17.45 |
| SK-MEL-2 | Melanoma | 105.56 | 14.66 | 11.58 |
| SK-MEL-28 | Melanoma | 93.27 | 4.54 | 29.70 |
| SK-MEL-5 | Melanoma | 100.45 | 6.11 | 7.01 |
| UACC-257 | Melanoma | 87.17 | 74.72 | 100.23 |
| UACC-62 | Melanoma | 46.28 | 8.26 | 4.85 |
| IGR-OV1 | Ovarian | 36.94 | 77.53 | 8.63 |
| OVCAR-3 | Ovarian | 48.69 | 95.45 | 16.81 |
| OVCAR-4 | Ovarian | 53.04 | 96.96 | 102.87 |
| OVCAR-5 | Ovarian | 76.83 | 104.07 | 57.14 |
| OVCAR-8 | Ovarian | 31.66 | 73.88 | 14.98 |
| NCI/ADR-RES | Ovarian | 93.28 | 98.95 | 78.81 |
| SK-OV-3 | Ovarian | 56.48 | 74.22 | 47.81 |
| 786-0 | Renal | 94.21 | 69.52 | 17.62 |
| A498 | Renal | 93.77 | 100.69 | 62.93 |
| ACHN | Renal | 23.28 | 77.77 | 40.21 |
| CAKI-1 | Renal | 86.77 | 46.83 | 0.00 |
| RXF 393 | Renal | 12.01 | 7.81 | 8.68 |
| SN12C | Renal | 42.15 | 25.78 | 45.36 |
| TK-10 | Renal | 88.53 | 73.91 | 35.87 |
| UO-31 | Renal | 19.66 | 3.37 | 28.19 |
| PC-3 | Prostate | 8.43 | 3.55 | 50.00 |
| DU-145 | Prostate | 29.78 | 11.24 | 72.47 |
| MCF7 | Breast | 89.78 | 108.31 | 69.14 |
| MDA-MB-231 | Breast | 48.51 | 33.90 | 41.84 |
| MDA-MB-468 | Breast | 101.73 | 93.85 | 45.81 |
| HS 578T | Breast | 53.92 | 50.13 | 51.47 |
| BT-549 | Breast | 103.01 | 79.20 | 62.51 |
| T-47D | Breast | 60.76 | 63.34 | 37.46 |
| MM1S | Multiple Myeloma | 52.32 | 58.17 | 26.41 |

Example 4

Inhibition of Viability of Acute Leukemia Cell Lines by Substituted Pyrrolo[2,3-d]Pyrimidine Compounds Compounds 381, 383, 409 (as test compounds) and Compound 501 (as a negative control) were administered to a variety of acute leukemia cell lines (THP-1. K562, Kasumi-1, and U937) in order to test their ability to inhibit cell growth as compared to 8-amino adenosine (8NH2-Ado) and 8-chloro adenosine (8Cl-Ado) (as positive controls) as in the previous Examples. The results are presented in FIGS. 11-14. All test compounds were found to reduce cell viability significantly, and Compound 381 and Compound 383 had inhibitory activities approaching those of 8NH2-Ado and 8Cl-Ado.

Figure 15:
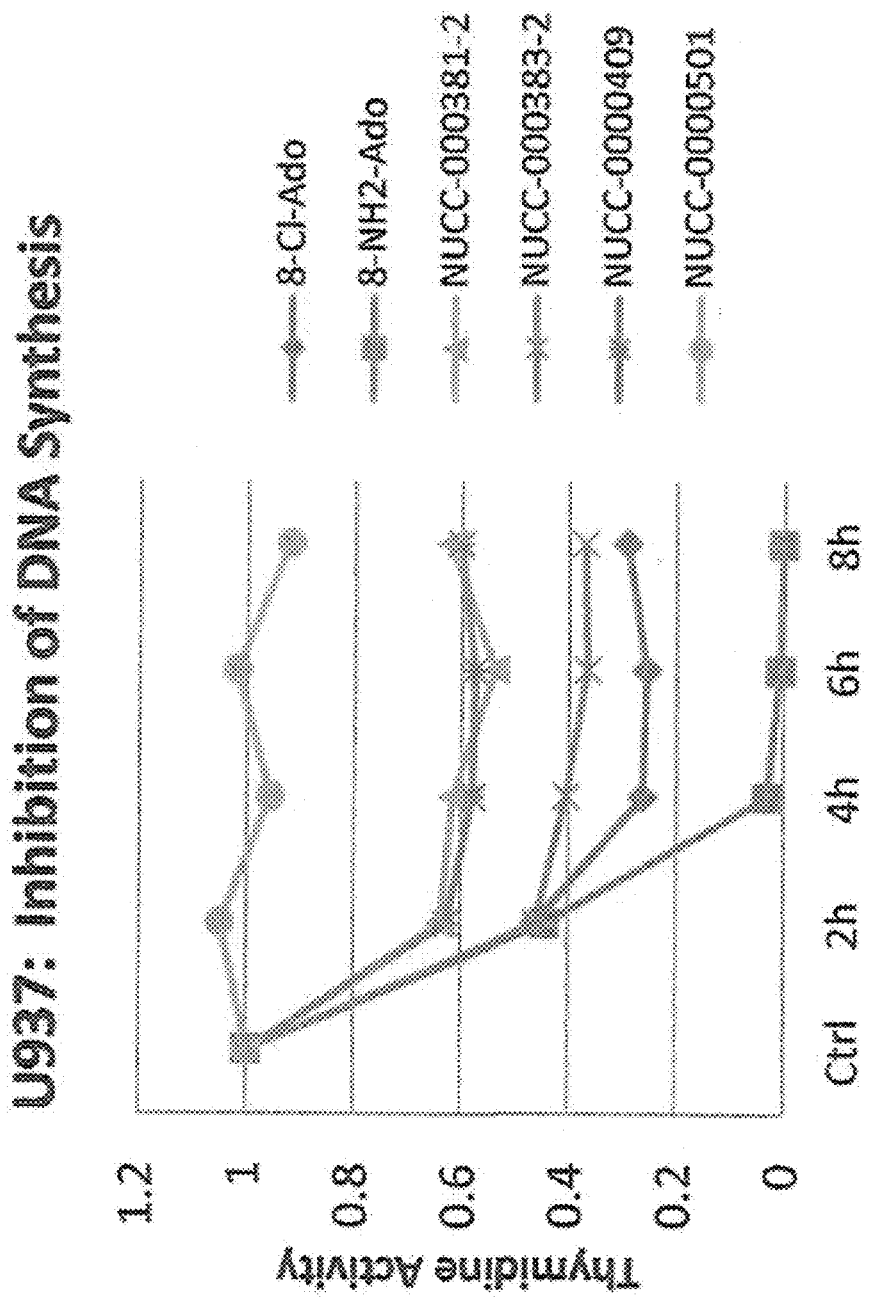
FIG. 15. Inhibition of RNA synthesis in U937 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).
Figure 16:
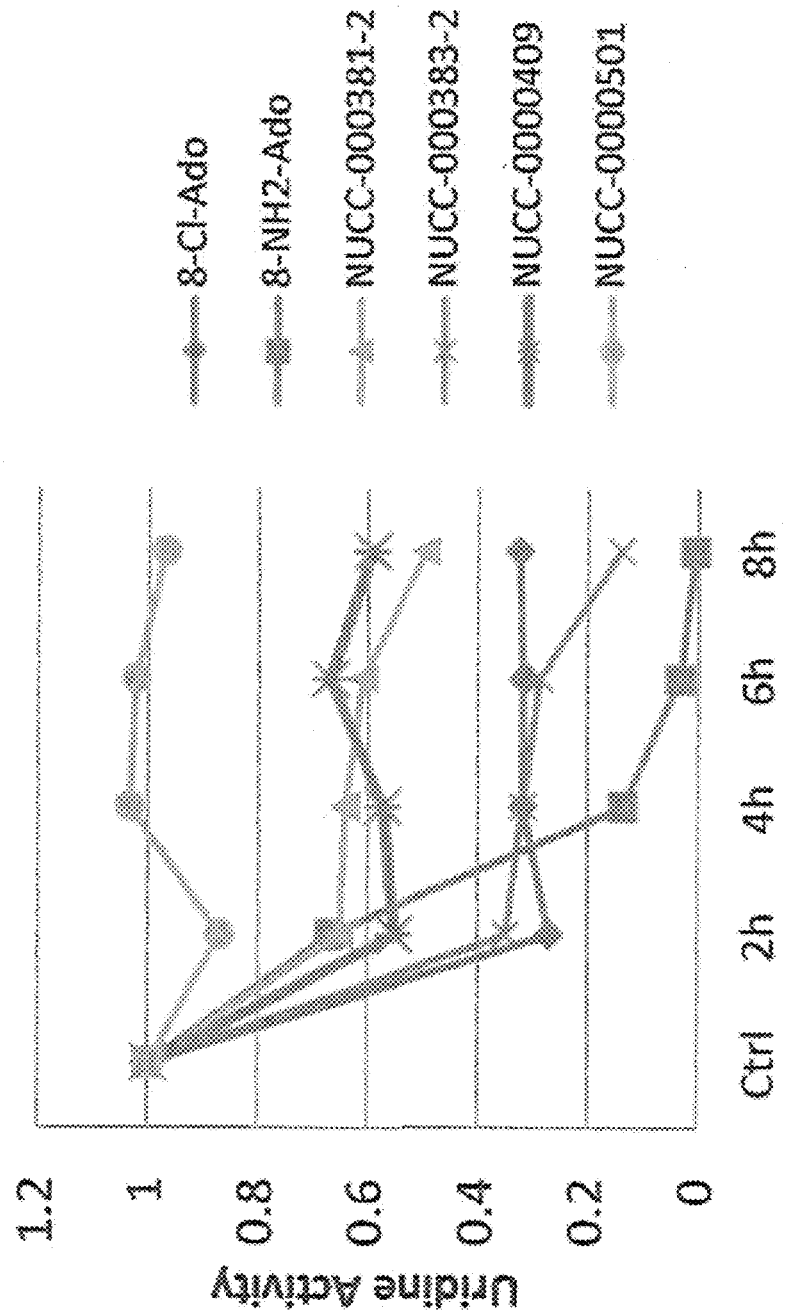
FIG. 16. Inhibition of RNA synthesis in U937 cell lines treated with Compounds 381, 383, 409 (as test compounds) and Compound 501 (as a negative control) as compared to 8-amino adenosine (8NH2-Ado) and 8-chloro adenosine (SCI-Ado) (as positive controls).

Compounds 381, 383, 409 (as test compounds) and Compound 501 (as a negative control) were administered to U937 cells in order to test their ability to inhibit DNA synthesis and RNA synthesis as compared to 8-amino adenosine (8NH2-Ado) and 8-chloro adenosine (8Cl-Ado) (as positive controls). In the test, the incorporated amount of tritiated labeled thymidine (for DNA synthesis) or tritiated labeled uridine (for RNA synthesis) by the U937 cells was measured over time. As illustrated in FIG. 15 and FIG. 16, the amount of incorporated label decreases over time indicating inhibition of both DNA and RNA synthesis.

Figure 17:
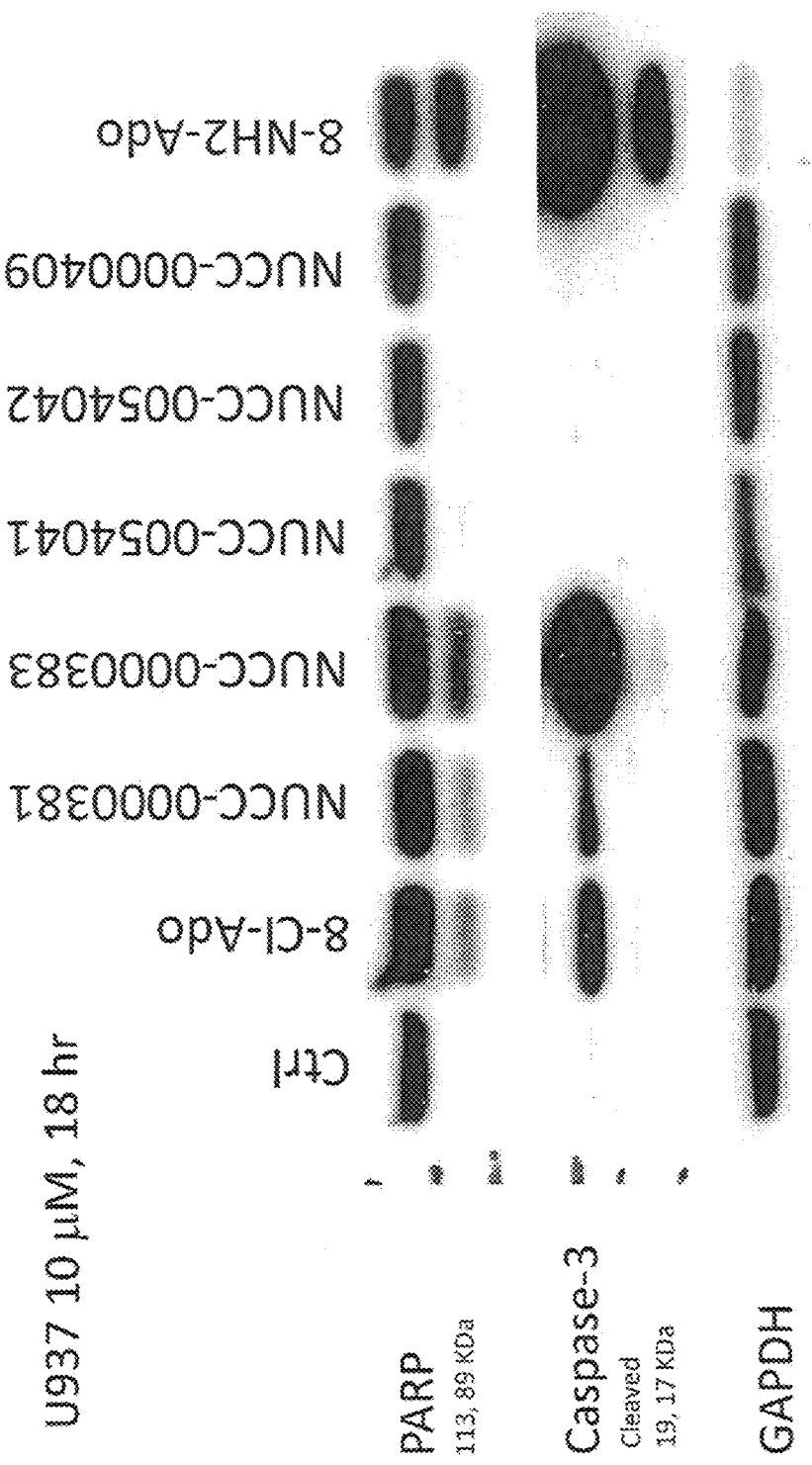
FIG. 17. Immunoblot of cell lysates from U937 cell lines treated with Compounds 381, 383, 409 (as test compounds) and Compound 501 (as a negative control) as compared to 8-amino adenosine (8NH2-Ado) and 8-chloro adenosine (8Cl-Ado) (as positive controls).

The impact of the compounds on proteins associated with cell death was assessed via performing an immunoblot. (See FIG. 17). PARP cleavage indicated activation of the caspase cascade and cell death by induction of apoptosis. Similarly detection of cleaved caspase 3 indicated activation of caspase activity and cell death by apoptosis. GAPDH was included as a loading control to indicate approximately equal loading of protein. Induction of apoptosis was observed for 8-Cl-Ado and 8-NH2-Ado (positive controls) and well as for Compounds 381 and 383.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having a Formula I:

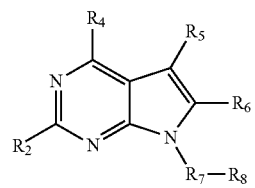

I wherein:
$R_2$ is hydrogen, halogen, or amino;
$R_4$ is hydrogen, halogen, amino, or $C_1$-$C_3$ alkyl optionally substituted at one or more positions with halogen;
$R_5$ and $R_6$ are each independently hydrogen, or $C_1$-$C_3$ alkyl optionally substituted at one or more positions with halogen; wherein at least one of $R_5$ and $R_6$ is trifluoromethyl;
$R_7$ is —$(CH_2)_n$— where n is 1 or 2;
$R_8$ is methoxy, amino, or a 4-, 5-, or 6-membered carbocyclic or heterocyclic ring that is saturated or unsaturated, the carbocyclic or heterocyclic ring optionally substituted at one or more carbon atoms with halogen, hydroxyl, methoxy, oxo, methylcarboxyl, methylamido, or methylhydroxyl; and the heterocyclic ring is optionally substituted at a nitrogen heteroatom with a substituent selected from $C_1$-$C_3$ alkyl,

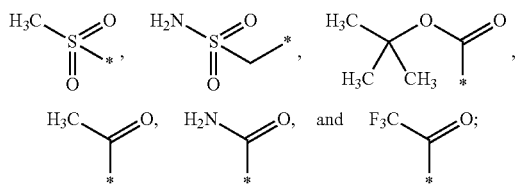

or $R_8$ is selected from

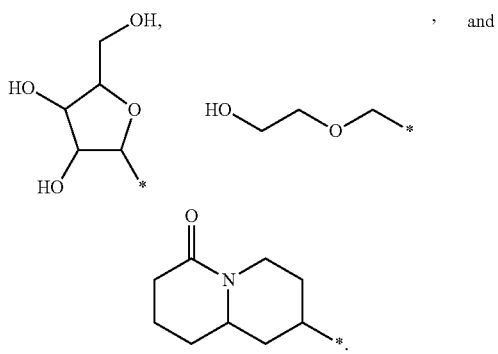

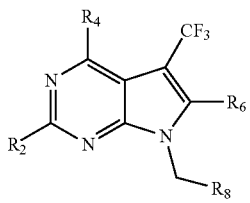

2. The compound of claim 1, wherein $R_4$ is halogen.
3. The compound of claim 2, wherein $R_4$ is chlorine.
4. The compound of claim 1 having a Formula IA:

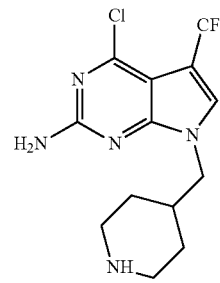

IA wherein: $R_2$, $R_4$, $R_6$, and $R_8$ are as defined for Formula I.

5. The compound of claim 4, wherein $R_8$ is a ring selected from piperidinyl, phenyl, pyridinyl, and oxanyl, which may be substituted at one or more carbon atoms with halogen or methoxy, and which may be substituted at a nitrogen heteroatom with a substituent selected from

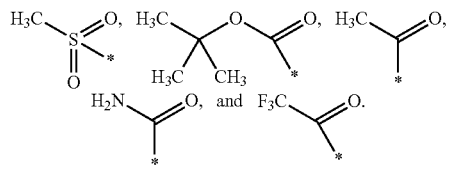

6. A compound having a formula selected from:

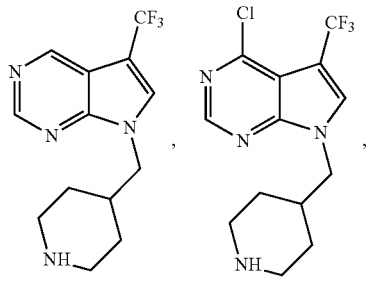

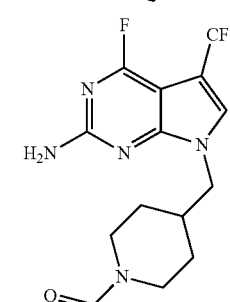

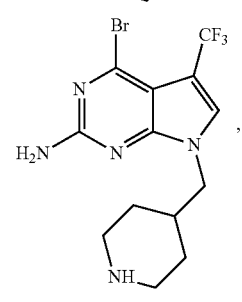

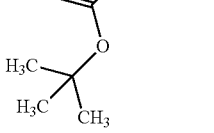

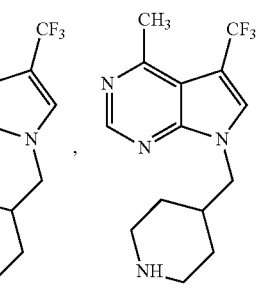

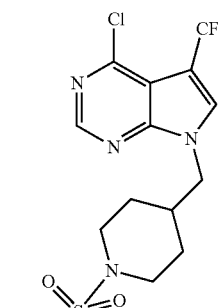

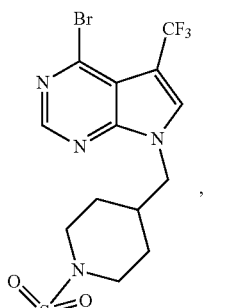

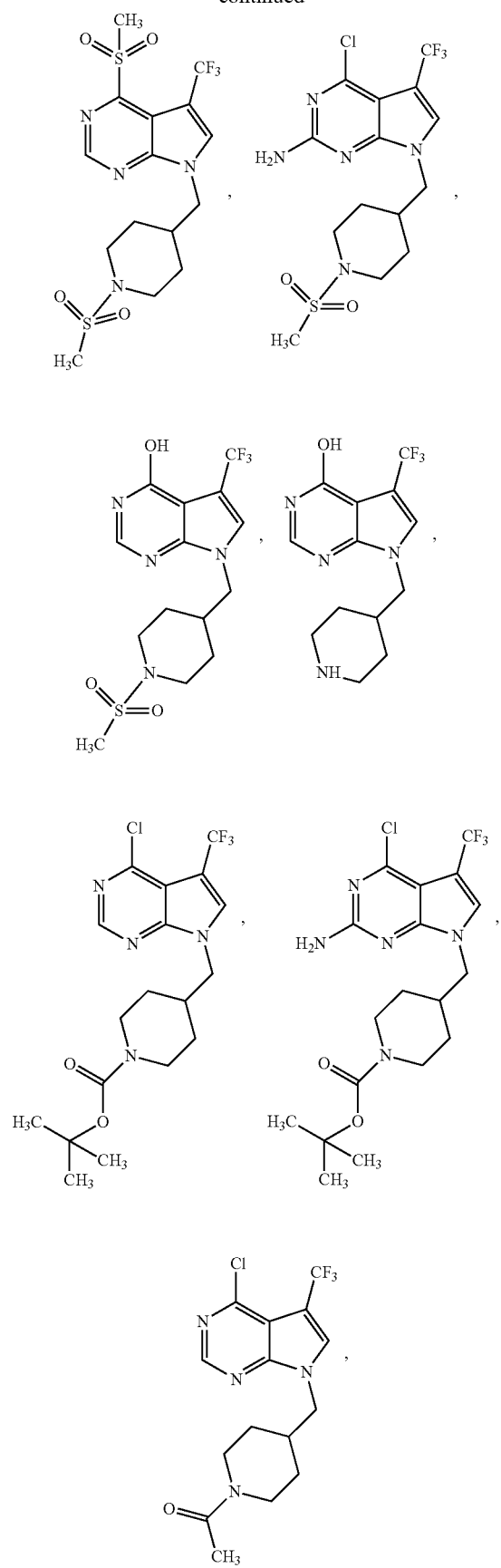
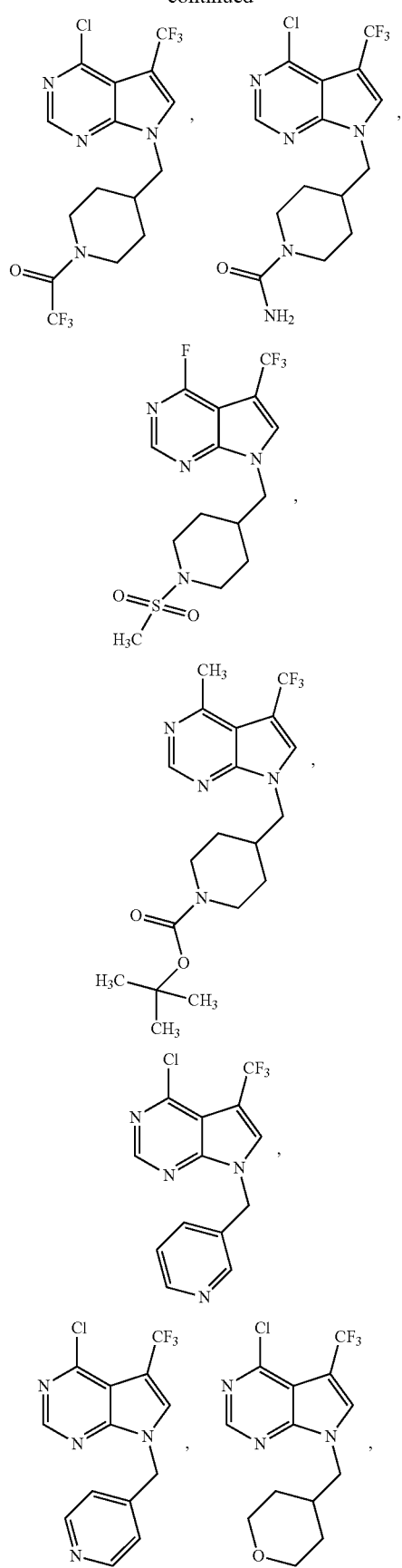

-continued

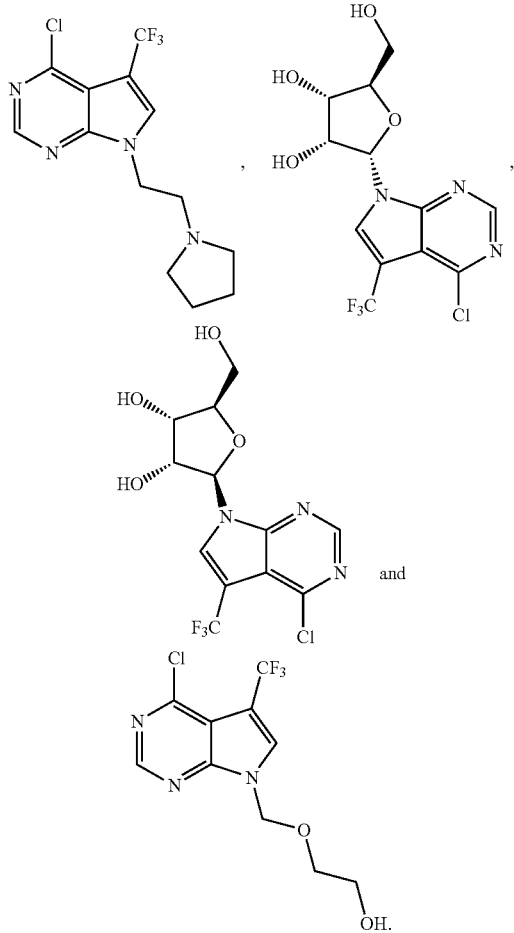

7. The compound of claim 1 having a Formula IB:

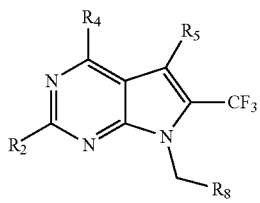

wherein: $R_2$, $R_4$, $R_6$, and $R_8$ are as defined for Formula I.

8. The compound of claim 7, wherein $R_8$ is a ring selected from piperidinyl, phenyl, pyridinyl, and oxanyl, which may be substituted at one or more carbon atoms with halogen or methoxy, and which may be substituted at a nitrogen heteroatom with a substituent selected from

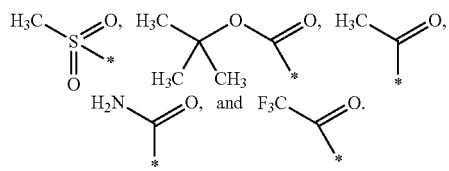

9. The compound of claim 7, having a formula selected from:

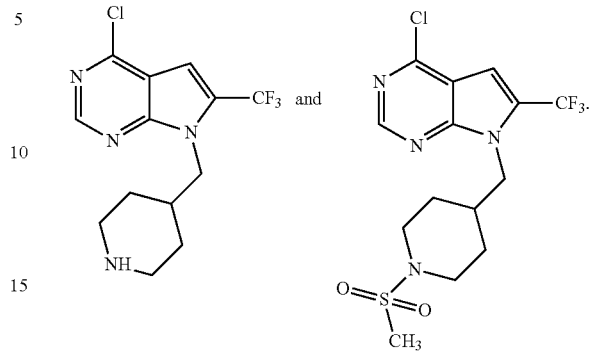

10. A pharmaceutical composition comprising an effective amount of the compound of claim 1 together with a carrier, excipient, or diluent.

11. A compound having a Formula I:

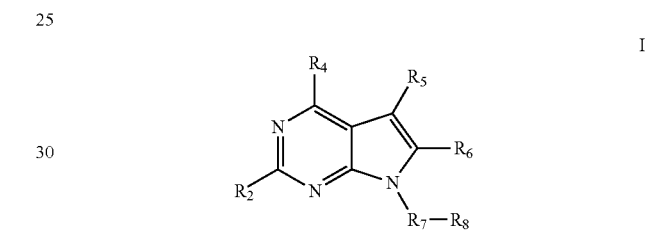

wherein:

$R_2$ is hydrogen, halogen, or amino;

$R_4$ is hydrogen, hydroxyl, halogen, acetyl, amino, methylsulfonyl, cyano, or $C_1$-$C_3$ alkyl optionally substituted at one or more positions with halogen;

$R_5$ and $R_6$ are each independently hydrogen, halogen, amino, or $C_1$-$C_3$ alkyl optionally substituted at one or more positions with halogen; wherein at least one of $R_5$ and $R_6$ is $C_1$-$C_3$ alkyl substituted at one or more positions with halogen;

$R_7$ is —$(CH_2)_n$— where n is 1, 2, or 3;

$R_8$ is hydrogen, $C_1$-$C_3$ alkyl optionally substituted at one or more positions with halogen, $C_1$-$C_3$ alkoxy, amino, or a saturated 4-, 5-, or 6-membered carbocyclic or heterocyclic ring, the carbocyclic or heterocyclic ring optionally substituted at one or more carbon atoms with halogen, hydroxyl, methoxy, oxo, methylcarboxyl, methylamido, or methylhydroxyl; and the heterocyclic ring is optionally substituted at a nitrogen heteroatom with a substituent selected from $C_1$-$C_3$ alkyl,

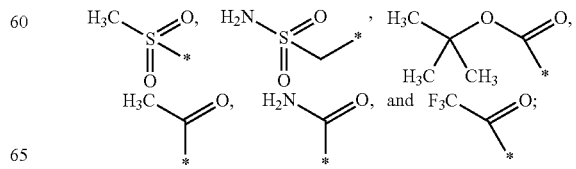

or
R<sub>8</sub> is selected from

[chemical structures: ribose-like furanose with OH groups; HO-CH2-CH2-O-CH2-*; and a bicyclic lactam structure]

12. A compound having a formula:

[structure I: pyrrolopyrimidine core with R<sub>4</sub>, R<sub>5</sub>, R<sub>2</sub>, R<sub>6</sub>, R<sub>7</sub>—R<sub>8</sub>]

wherein:
R<sub>2</sub> is hydrogen, halogen, or amino;
R<sub>4</sub> is hydrogen, hydroxyl, halogen, acetyl, amino, methylsulfonyl, cyano, or $C_1$-$C_3$ alkyl optionally substituted at one or more positions with halogen;
R<sub>5</sub> and R<sub>6</sub> are each independently hydrogen, amino, or $C_1$-$C_3$ alkyl optionally substituted at one or more positions with halogen;
R<sub>7</sub> is —(CH<sub>2</sub>)—;
R<sub>8</sub> is piperidin-4-yl optionally substituted at the nitrogen heteroatom with a substituent selected from

[chemical substituent structures: methylsulfonyl, Boc (tert-butoxycarbonyl), acetyl, carbamoyl, and trifluoroacetyl groups]

13. The compound of claim 12, having a formula selected from:

[two structures: 4-bromo-5-methyl-pyrrolopyrimidine with piperidinylmethyl; 4-chloro-5-methyl-2-amino-pyrrolopyrimidine with piperidinylmethyl]

[continued: 4-chloro-5-methyl-2-amino-pyrrolopyrimidine with N-methylsulfonyl piperidinylmethyl; and 4-chloro-5-methyl-pyrrolopyrimidine with N-Boc piperidinylmethyl]

14. The compound of claim 12 having a Formula IF:

[structure IF: pyrrolopyrimidine with R<sub>2</sub>, R<sub>4</sub>, and N-piperidinylmethyl with R<sub>9</sub>]

wherein:
R<sub>2</sub> is hydrogen, halogen, or amino;
R<sub>4</sub> is halogen; and
R<sub>9</sub> is hydrogen, or R<sub>9</sub> is selected from

[chemical substituent structures: methylsulfonyl, acetyl, and Boc groups]

15. The compound of claim 14, having a formula selected from:

[structure: 2,4-dichloro-pyrrolopyrimidine with piperidinylmethyl (NH)]

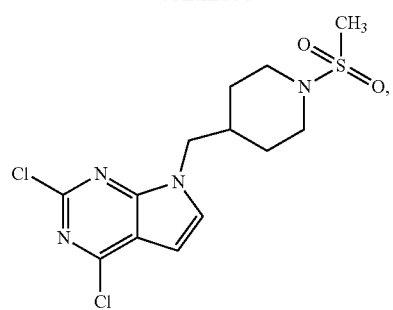
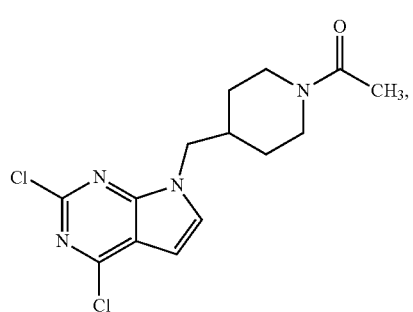
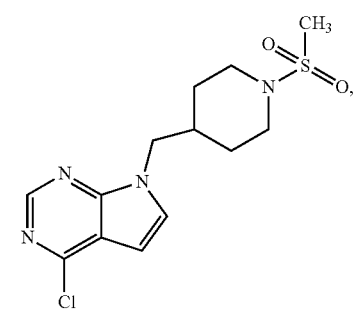
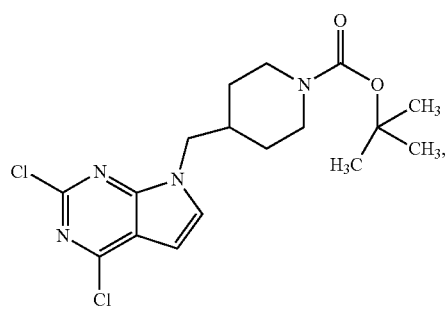

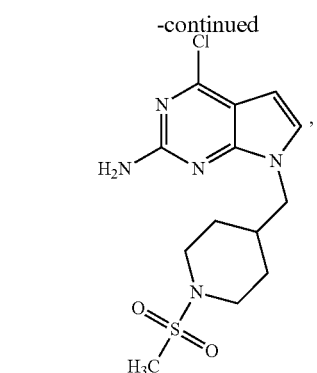
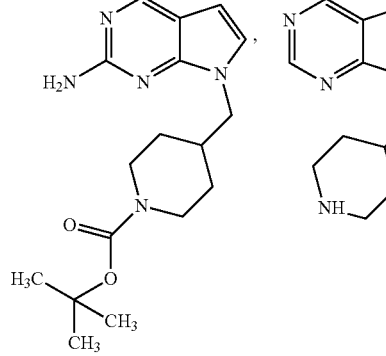
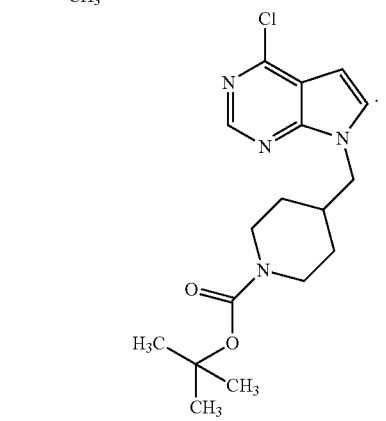

16. A pharmaceutical composition comprising an effective amount of the compound of claim 6 together with a carrier, excipient, or diluent.

17. A pharmaceutical composition comprising an effective amount of the compound of claim 11 together with a carrier, excipient, or diluent.

18. A pharmaceutical composition comprising an effective amount of the compound of claim 12 together with a carrier, excipient, or diluent.

* * * * *